US009514713B2

(12) United States Patent
Lee et al.

(10) Patent No.: US 9,514,713 B2
(45) Date of Patent: Dec. 6, 2016

(54) TIMING CONTROLLER, SOURCE DRIVER, AND DISPLAY DRIVER INTEGRATED CIRCUIT HAVING IMPROVED TEST EFFICIENCY AND METHOD OF OPERATING DISPLAY DRIVING CIRCUIT

(71) Applicant: SAMSUNG ELECTRONICS CO., LTD., Suwon-Si, Gyeonggi-Do (KR)

(72) Inventors: Dong-Myung Lee, Yongin-Si (KR); Young-Min Choi, Yongin-Si (KR); Jae-Youl Lee, Hwaseong-Si (KR); Han-Su Pae, Seongnam-Si (KR); Dong-Hoon Baek, Seoul (KR); Young-Hun Lee, Seoul (KR); Kil-Hoon Lee, Seoul (KR)

(73) Assignee: SAMSUNG ELECTRONICS CO., LTD., Suwon-Si, Gyeonggi-Do (KR)

( * ) Notice: Subject to any disclaimer, the term of this patent is extended or adjusted under 35 U.S.C. 154(b) by 91 days.

(21) Appl. No.: 14/455,484

(22) Filed: Aug. 8, 2014

(65) Prior Publication Data

US 2015/0154943 A1 Jun. 4, 2015

(30) Foreign Application Priority Data

Dec. 3, 2013 (KR) ........................ 10-2013-0149493

(51) Int. Cl.

| | |
|---|---|
| ***G09G 3/00*** | (2006.01) |
| ***G09G 3/20*** | (2006.01) |
| ***G09G 3/36*** | (2006.01) |
| ***H04N 5/335*** | (2011.01) |
| ***H04N 19/70*** | (2014.01) |
| ***H03M 1/10*** | (2006.01) |
| ***A61K 31/40*** | (2006.01) |

(Continued)

(52) U.S. Cl.
CPC ................ *G09G 5/18* (2013.01); *G09G 5/006* (2013.01); *G09G 2340/02* (2013.01); *G09G 2370/08* (2013.01)

(58) Field of Classification Search
CPC . G09G 2370/08; G09G 3/3655; H04N 21/242
See application file for complete search history.

(56) References Cited

U.S. PATENT DOCUMENTS 3,775,747 A * 11/1973 Gabriel .................. H03M 1/10 341/164
5,872,597 A * 2/1999 Yamakage ............ H04N 19/70 348/699

(Continued)

FOREIGN PATENT DOCUMENTS

JP 2006-251924 9/2006
JP 2009-003155 1/2009

(Continued)

*Primary Examiner* — Lin Li
(74) *Attorney, Agent, or Firm* — F. Chau & Associates, LLC

(57) ABSTRACT

A timing controller, a source driver, and a display driver integrated circuit (DDI) having improved test efficiency and a method of operating the DDI are provided. The timing controller includes a code generation unit for generating a first code from display data, a protocol encoder for generating a data sequence including the display data and the first code, and a transmission unit for providing the data sequence to a source driver through a link.

20 Claims, 26 Drawing Sheets

(51) Int. Cl.
*G09G 5/18* (2006.01)
*G09G 5/00* (2006.01)

(56) References Cited

U.S. PATENT DOCUMENTS

| | | | | |
|---|---|---|---|---|
| 6,697,106 | B1 * | 2/2004 | Saito | H04N 5/335 348/222.1 |
| 7,471,302 | B2 | 12/2008 | Fukuda et al. | |
| 7,961,169 | B2 | 6/2011 | Oh | |
| 2005/0163116 | A1 * | 7/2005 | Anderson | H04L 29/06027 370/389 |
| 2005/0200590 | A1 | 9/2005 | Kumekawa | |
| 2007/0164969 | A1 * | 7/2007 | Kim | G09G 3/3611 345/99 |
| 2007/0279361 | A1 * | 12/2007 | Shin | G09G 3/2092 345/98 |
| 2008/0012809 | A1 * | 1/2008 | Kim | G09G 3/3648 345/87 |
| 2009/0177930 | A1 * | 7/2009 | Park | G09G 3/2003 714/49 |
| 2010/0231614 | A1 * | 9/2010 | Vieri | G09G 3/3677 345/690 |
| 2011/0118235 | A1 * | 5/2011 | Howbert | A61K 31/4025 514/213.01 |
| 2011/0292024 | A1 * | 12/2011 | Baek | G09G 3/2096 345/212 |
| 2012/0036418 | A1 | 2/2012 | Morino et al. | |
| 2012/0146965 | A1 * | 6/2012 | Baek | G09G 3/006 345/204 |
| 2012/0166896 | A1 | 6/2012 | Oh et al. | |
| 2012/0218317 | A1 * | 8/2012 | Choi | G09G 3/3655 345/690 |
| 2012/0242628 | A1 * | 9/2012 | Yuan | G09G 3/20 345/204 |
| 2013/0036335 | A1 | 2/2013 | Kim et al. | |
| 2013/0057530 | A1 * | 3/2013 | Han | G09G 3/3696 345/211 |
| 2014/0118235 | A1 * | 5/2014 | Hong | G09G 5/008 345/87 |

FOREIGN PATENT DOCUMENTS

| | | |
|---|---|---|
| KR | 10-2007-0080170 | 8/2007 |
| KR | 10-2012-0065840 | 6/2012 |

* cited by examiner

FIG. 8A
SOL
CRC EN
RD EN
DSP Data
HBP

FIG. 15B
SOL
CRC EN
VCRC EN
DSP Data
CRC Data
HBP

TIMING CONTROLLER, SOURCE DRIVER, AND DISPLAY DRIVER INTEGRATED CIRCUIT HAVING IMPROVED TEST EFFICIENCY AND METHOD OF OPERATING DISPLAY DRIVING CIRCUIT

CROSS-REFERENCE TO RELATED APPLICATION

This application claims under 35 U.S.C. §119(a) priority to and the benefit of Korean Patent Application No. 10-2013-0149493, filed on Dec. 3, 2013, in the Korean Intellectual Property Office, the entire content of which is incorporated by reference herein.

BACKGROUND

The present disclosure relates to a display driver integrated circuit (DDI), and, more particularly, to a timing controller, a source driver, and a DDI having improved test efficiency and a method of operating the DDI.

In general, to provide a screen output, flat display apparatuses, such as a liquid crystal display (LCD), an organic light-emitting diode (OLED) display, and the like, are widely used. A flat display apparatus includes a panel in which a plurality of pixels are arranged to realize an image. A DDI provides a data signal (display data) to drive the pixels in the panel to realize an image.

The display data and various kinds of control signals can be provided to the panel through one or more links, but since an error can occur in signal transmission through the links, a bit error rate test (BERT) can be performed to check whether an error occurs in the signal transmission. For example, a panel having a large size and high resolution can have long links for transmitting signals therethrough, and in this case, the possibility of a signal transmission error can be high. However, to perform a test operation, a separate device for generating a test pattern, a separate test time, and the like, is typically required, thereby decreasing the efficiency according to the test process.

SUMMARY

Exemplary embodiments of the inventive concept provide a timing controller, a source driver, and a display driver integrated circuit (DDI) having improved test efficiency and a method of operating the DDI.

According to an exemplary embodiment of the inventive concept, there is provided a timing controller including a code generation unit for generating a first code from display data, a protocol encoder for generating a data sequence including the display data and the first code, and a transmission unit for providing the data sequence to a source driver through a link.

The data sequence may further include first information for enabling a data error detection operation using the first code.

The code generation unit may be a cyclic redundancy check (CRC) encoder for generating CRC data from the display data.

The timing controller may sequentially provide display data for a screen output with respect to a plurality of gate lines included in a panel to the source driver, and the code generation unit may generate the first code in correspondence with display data for each gate line.

The timing controller may sequentially provide display data for a screen output with respect to a plurality of gate lines included in a panel to the source driver and receive a data error detection result using the first code from the source driver after providing the display data for the plurality of gate lines.

The timing controller may further include a reception unit for receiving a data error detection result using the first code from the source driver, and a data control unit for controlling a combination of the display data and test data according to the data error detection result.

The timing controller may be connected to a plurality of source drivers through different links and simultaneously provide the data sequence to the plurality of source drivers.

According to another exemplary embodiment of the inventive concept, there is provided a source driver including a protocol decoder for receiving a data sequence including display data and a first code corresponding to the display data and decoding the received data sequence, and an error detection unit for performing an error detection operation on the display data by using the first code included in the data sequence and a second code generated from the display data.

According to another exemplary embodiment of the inventive concept, there is provided a display driver integrated circuit (DDI) including a timing controller for generating a first code from display data and outputting a data sequence including the display data and the first code, and a source driver for receiving the data sequence through a first link, generating a second code corresponding to the display data and performing an error detection operation on the display data by using the first code included in the data sequence and the generated second code.

According to another exemplary embodiment of the inventive concept, there is provided a method of operating a display driver integrated circuit (DDI). The method includes generating a first code corresponding to first display data, enabling first information indicating a request for error detection using the first code and the first display data, generating a data sequence including the first information, the first code and the first display data, and providing the data sequence to a source driver through a main link between a timing controller and the source driver.

BRIEF DESCRIPTION OF THE DRAWINGS

Exemplary embodiments of the inventive concept will be more clearly understood from the following detailed description taken in conjunction with the accompanying drawings in which.

DETAILED DESCRIPTION OF THE EMBODIMENTS

To fully understand the inventive concept, operational advantages of the inventive concept, and objects obtained by embodiments of the inventive concept, the attached drawings and contents written in the attached drawings must be referred.

The inventive concept will now be described more fully with reference to the accompanying drawings, in which exemplary embodiments of the inventive concept are shown. Like reference numbers are used to refer to like elements throughout the drawings.

As used herein, the term "and/or" includes any and all combinations of one or more of the associated listed items. Expressions such as "at least one of," when preceding a list of elements, modify the entire list of elements and do not modify the individual elements of the list.

Figure 1:
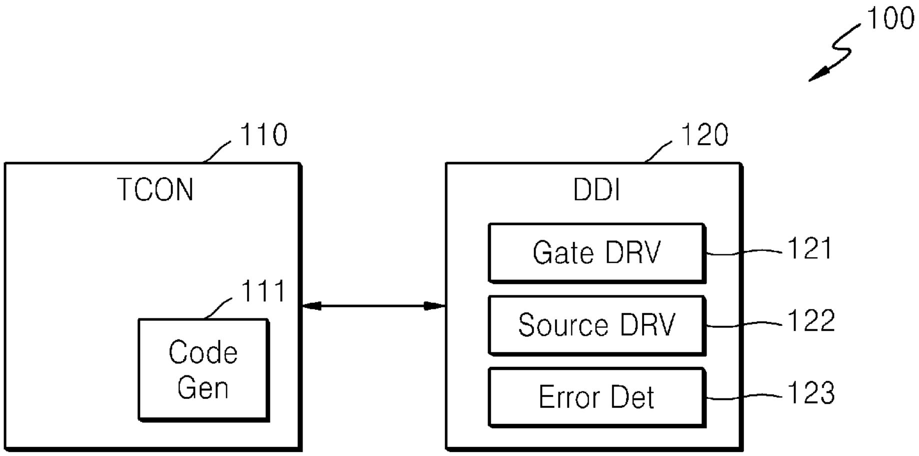
FIG. 1 is a block diagram of a display apparatus according to an exemplary embodiment of the inventive concept.

FIG. 1 is a block diagram of a display apparatus 100 according to an exemplary embodiment of the inventive concept. As shown in FIG. 1, the display apparatus 100 may include a timing controller (TCON) 110 and a display driver integrated circuit (DDI) 120.

A DDI may be defined in various forms and may include, for example, a gate driver for driving a gate line, a source driver for driving a data line of a panel, and the like. For example, in a display apparatus having a large-size panel, a TCON, a gate driver, a source driver, and the like may be implemented as separate chips. In FIG. 1, it is assumed that the DDI 120 includes a gate driver 121 and a source driver 122, and that the TCON 110 and the DDI 120 transmit or receive various signals.

As shown in FIG. 1, for a test operation on the display apparatus 100, the TCON 110 may include a code generation unit 111, and the DDI 120 may include an error detection unit 123. The test operation may be performed according to various types. For example, a test operation on pixels in a panel may be performed, or a signal delay on a transmission path (e.g., main link) between the TCON 110 and the DDI 120, or an error due to electromagnetic interference, may be tested. According to one or more exemplary embodiments of the inventive concept, a test may be performed through a normal display operation without generating a separate test mode or a test pattern for a test operation, and may be performed by performing an error detection operation using normal display data.

The code generation unit 111 may receive display data from an external host (not shown), generate a packet having a predetermined format through a protocol encoding operation on the display data, and provide the generated packet to the DDI 120. The display data and various kinds of information according to a protocol may be included in the packet through the protocol encoding operation, and the generated packet may be transmitted to the DDI 120 through the main link.

The code generation unit 111 may generate a code, e.g., an error detection code, from the display data. The error detection code may be included in a data sequence and provided to the DDI 120. The code generation unit 111 may generate various kinds of error detection codes to be used for error detection and correction, such as an error detection code for detecting a one-bit error or an error detection code for detecting a two or more-bit error in correspondence with one error correction unit. For example, the code generation unit 111 may generate any one error detection code selected from a set of a parity code, a cyclic redundancy check (CRC) code, a Hamming code, an error correction circuit (ECC) code, and the like from the display data. A kind of an error detection code may be selected according to an error detection algorithm applied to a test. According to one or more exemplary embodiments of the inventive concept, other kinds of error detection codes with which an error detection operation is performed may be applied.

A data sequence, including the error detection code, is transmitted to the DDI 120 through a link. The error detection unit 123 performs an error detection operation on the display data by using the display data and the error detection code included in the data sequence. FIG. 1 shows function blocks, wherein the source driver 122 and the error detection unit 123 are separate. However, the data sequence is information including normal display data and may be provided to the source driver 122, and accordingly, though not shown, the error detection unit 123 may be included in the source driver 122 and may perform an error detection operation by using the data sequence received by the source driver 122.

As described above, the data sequence may further include various kinds of information according to a transmission protocol. For example, when the error detection code is included in the data sequence, first information for requesting enabling an error detection operation on the display data may be further included in the data sequence. The first information may be extracted through a protocol decoding operation, and the error detection unit 123 may perform an error detection operation in response to the extracted first information.

As described above, a test on a link may be performed using normal display data and an error detection code corresponding to the normal display data, and thus, the TCON 110 does not have to include a separate test pattern generator for a test operation. In addition, since the test on a link may be performed together with a normal display operation, a separate test mode for a test operation is not required, and thus, the time taken to perform the test operation may be reduced, thereby improving test efficiency.

Figure 2:
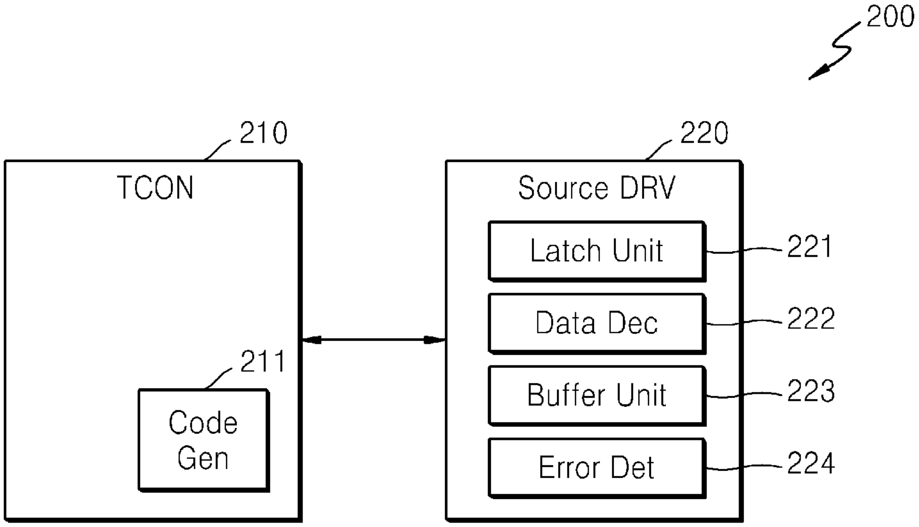
FIG. 2 is a block diagram of a display driver integrated circuit (DDI) according to an exemplary embodiment of the inventive concept.

FIG. 2 is a block diagram of a DDI 200 according to an exemplary embodiment of the inventive concept. As described above, a DDI may be defined in various forms, and as shown in FIG. 2, it may be defined where a TCON is included in a DDI. In FIG. 2, the DDI 200 includes a TCON 210 and a source driver 220.

The TCON 210 may include a code generation unit 211. The code generation unit 211 may generate an error detection code from display data, as described above. The TCON 210 may transmit a packet, including a data sequence, through a protocol encoding operation to the source driver 220 through a link. In addition, as described above, the data sequence may include the display data and the error detection code corresponding to the display data.

The source driver 220 may include a latch unit 221, a data decoder 222, a buffer unit 223, and an error detection unit 224. The latch unit 221 may temporarily store the display data from the TCON 210, and the data decoder 222 may decode and convert the display data provided as a digital signal into pixel data having an analog voltage. The buffer unit 223 may transmit the pixel data to a panel (not shown) through a data line, and the error detection unit 224 may perform an error detection operation on the display data by using the display data and the error detection code, as described above.

A test on the link may be performed according to the above-described error detection operation. The link may include various kinds of links. For example, as shown in FIG. 2, a test on a main link between the TCON 210 and the source driver 220 for transmitting the data sequence may be performed. The main link may perform bidirectional transmission of information, and an error detection result may be provided from the source driver 220 to the TCON 210 through the main link. The TCON 210 may control the source driver 220 on the basis of the received error detection result and the error detection result is displayed on the panel. In addition, the source driver 220 may optimize options therein by using the error detection result to thereby minimize errors in data sequence reception.

Figure 3:
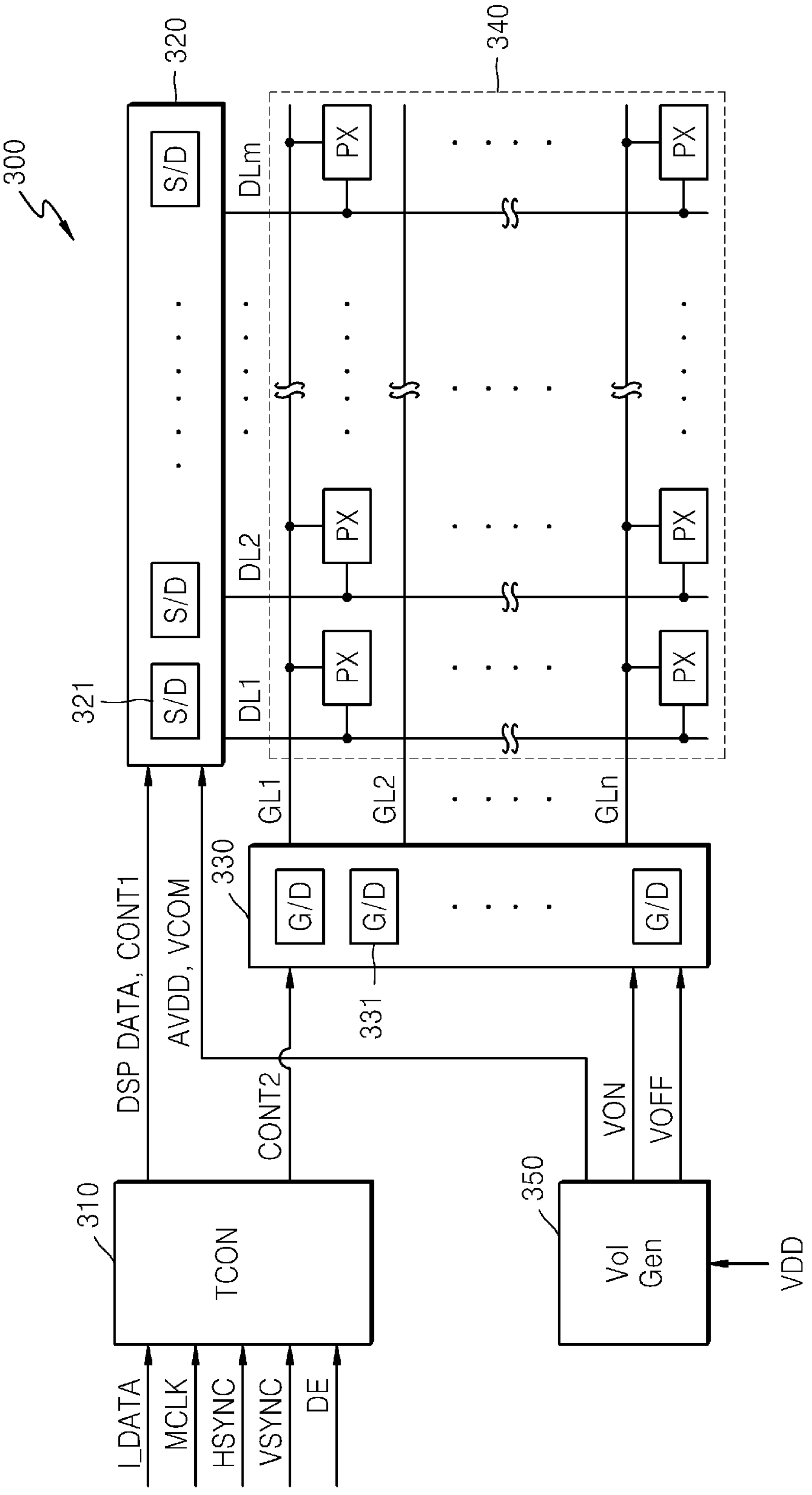
FIG. 3 is a block diagram of a display apparatus including a DDI, according to an exemplary embodiment of the inventive concept.

FIG. 3 is a block diagram of a display apparatus 300 including a DDI, according to an exemplary embodiment of the inventive concept. As described above, the DDI is a component arranged to drive a panel, and may include a source driver, a gate driver and a TCON.

As shown in FIG. 3, the display apparatus 300 includes a panel 340 for displaying an image and the DDI for driving the panel 340. The DDI may include a source driver (S/D) unit 320 for driving first to mth data lines DL1, DL2, . . . DLm of the panel 340, a gate driver (G/D) unit 330 for driving first to nth gate lines GL1, GL2, . . . GLn of the panel 340, a TCON 310 for generating various kinds of timing signals and data DSP DATA, CONT1, CONT2, and a voltage generation unit 350 for generating various kinds of voltages VON, VOFF, AVDD, VCOM required for display driving.

The display apparatus 300 may be applied to any one of various flat display apparatuses. For example, a flat display apparatus may include a liquid crystal display (LCD), an organic light-emitting diode (OLED) display, a plasma display panel (PDP), and the like, and the display apparatus 300 according to the current exemplary embodiment may be applied to any one of the flat display apparatuses. For convenience of description, hereinafter, an LCD apparatus will be described as an example.

The panel 340 includes the first to nth gate lines GL1 to GLn, the first to mth data lines DL1 to DLm arranged in a direction crossing the first to nth gate lines GL1 to GLn, and pixels PX arranged at locations where the first to nth gate lines GL1 to GLn and the first to mth data lines DL1 to DLm cross each other. When the display apparatus 300 is an LCD apparatus, each pixel PX may include a transistor having a gate and a source respectively connected to a gate line and a data line, an LCD capacitor connected to a drain of the transistor, and a storage capacitor.

The S/D unit 320 may include one or more S/Ds 321. For example, when the panel 340 has a large size, a plurality of S/Ds 321 may be provided, and one or more data lines may be driven by the S/Ds 321. The G/D unit 330 may also include one or more G/Ds 331, a plurality of G/Ds 331 may be provided in the G/D unit 330, and one or more gate lines may be driven by the G/Ds 331.

The TCON 310 receives external data I_DATA, a horizontal synchronization signal HSYNC, a vertical synchronization signal VSYNC, a clock signal MCLK, a data enable signal DE, and the like, that are input from an external device (or an external host). The TCON 310 generates display data DSP DATA of which a protocol has been converted so as to meet the interface specification with the S/D unit 320, and outputs the display data DSP DATA to the S/D unit 320. In addition, the TCON 310 generates various kinds of control signals for controlling timing of the S/D unit 320 and the G/D unit 330, outputs one or more first control signals CONT1 to the S/D unit 320, and outputs one or more second control signals CONT2 to the G/D unit 330. The voltage generation unit 350 receives a power source voltage VDD from the outside and generates various voltages required for an operation of the display apparatus 300. For example, the voltage generation unit 350 may generate a gate-on voltage VON and a gate-off voltage VOFF, and output the gate-on voltage VON and the gate-off voltage VOFF to the G/D unit 330. The voltage generation unit 350 may also generate an analog power source voltage AVDD and a common voltage VCOM, and output the analog power source voltage AVDD and the common voltage VCOM to the S/D unit 320.

The display data DSP DATA and the various kinds of timing signals CONT1, CONT2 output from the TCON 310 may be provided to the G/D unit 330 and the S/D unit 320 through main links. Although FIG. 3 shows only one line between the TCON 310 and the G/D unit 330 and only one line between the TCON 310 and the S/D unit 320, the display data DSP DATA and the various kinds of timing signals CONT1 and CONT2 output from the TCON 310 may be actually provided to the G/D unit 330 and the S/D unit 320 through a plurality of main links. For example, when a plurality of S/Ds 321 are provided, the TCON 310 may transmit the display data DSP DATA and the timing signal CONT1 to the plurality of S/Ds 321 through different main links.

The main links for transmitting signals between the TCON 310 and the plurality of S/Ds 321 may have different lengths. When the panel 340 has a large size, the main links may also have long lengths, and thus in signal transmission through a main link, an error due to a delay or electromagnetic interference may occur. Accordingly, a test (e.g., a bit error rate test (BERT)) on the main links for transmitting signals to the plurality of S/Ds 321 may be performed.

A test operation according to an exemplary embodiment of the inventive concept will now be described in detail with reference to FIGS. 4A, 4B, and 5.

Figure 4A:
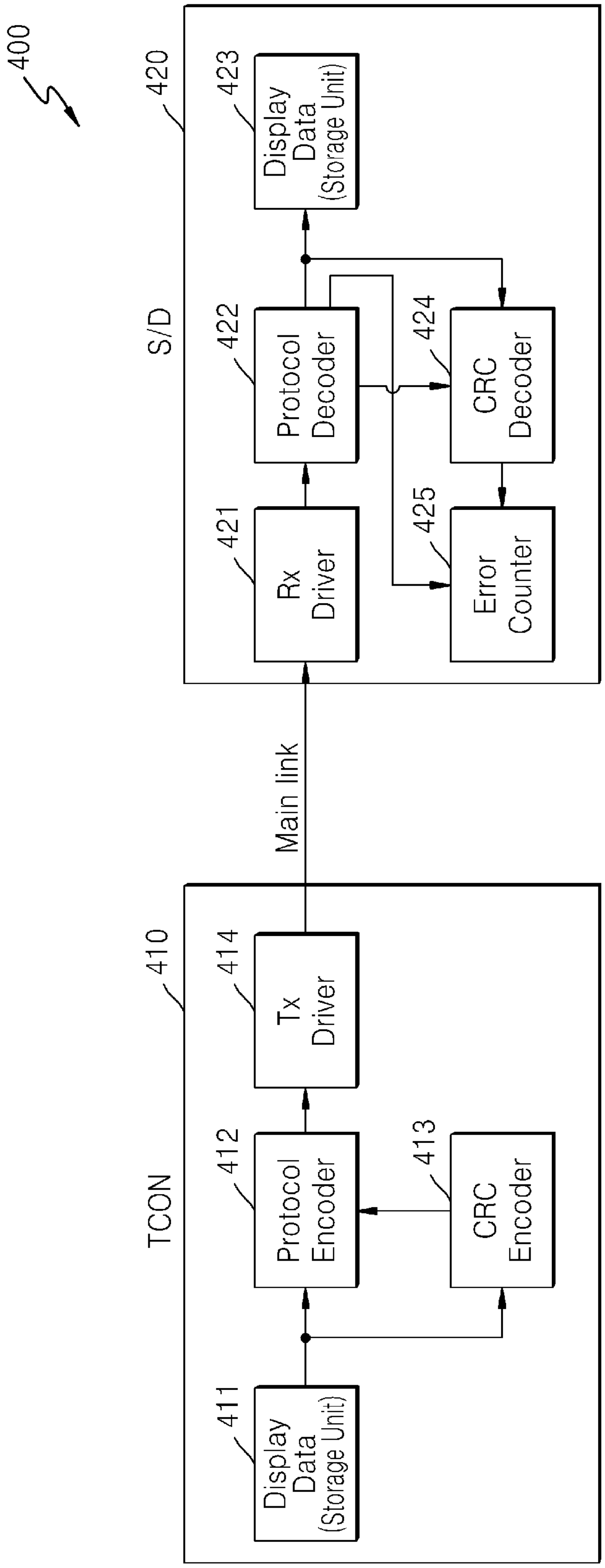
FIGS. 4A and 4B are block diagrams of a DDI according to an exemplary embodiment of the inventive concept.
Figure 4B:
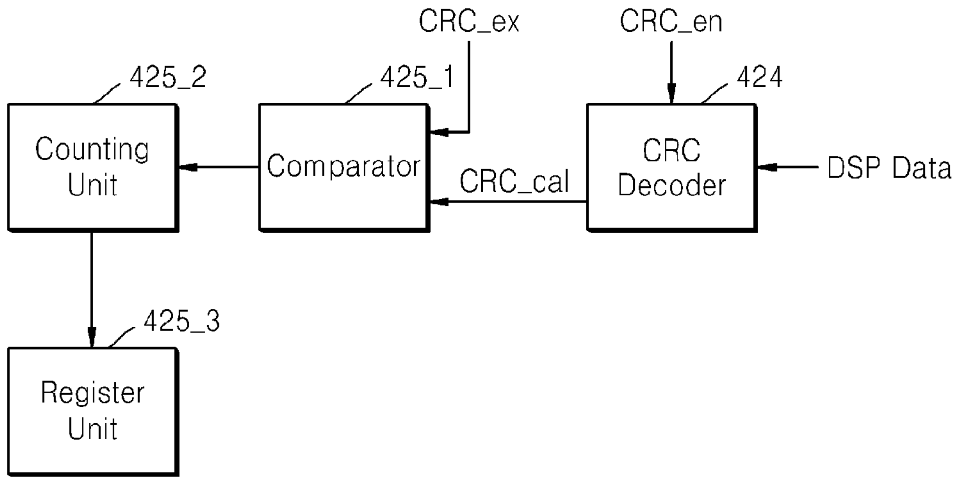
Figure 5:
FIG. 5 is a data format of a packet including a data sequence.

FIGS. 4A and 4B are block diagrams of a DDI 400 according to an exemplary embodiment of the inventive concept, and FIG. 5 is a data format of a packet including a data sequence. Hereinafter, it is assumed that the DDI 400 includes a TCON 410. In addition, a plurality of S/Ds may be arranged to drive a panel, and in FIG. 4A, only one S/D 420 is shown. In addition, it is assumed that an error detection code generated according to an exemplary embodiment of the inventive concept is a CRC code.

The DDI 400 may include the TCON 410 and the S/D 420. In addition, the TCON 410 may include a storage unit 411 for temporarily storing display data, a protocol encoder 412 for converting data according to a transmission protocol, a transmission (Tx) driver 414 for transmitting a packet including a data sequence, and a CRC encoder 413 for generating an error detection code from the display data.

The TCON 410 generates data for a normal display operation according to data from the outside. For example, the protocol encoder 412 generates a packet including a data sequence suitable for a transmission protocol. The CRC encoder 413 receives display data, generates a CRC code (hereinafter, referred to as CRC data) from the display data, and outputs the CRC data to the protocol encoder 412. The protocol encoder 412 generates a packet, including the display data and the CRC data, as a data sequence.

As shown in FIG. 5, a data sequence may include display data DSP Data, CRC data CRC Data, and one or more pieces of information. The one or more pieces of information may include error detection enabling information CRC EN for requesting to perform an error detection operation using the display data DSP Data and the CRC data CRC Data. In addition, the data sequence may further include a line start signal SOL indicating that data corresponding to one line is transmitted, a waiting signal HBP indicating a transmission waiting time, and the like, as other pieces of information.

The packet from the TCON 410 is provided to the S/D 420 through a main link. The S/D 420 may include a reception (Rx) driver 421, a protocol decoder 422, a data storage unit 423, a CRC decoder 424, and an error counter 425. The error detection unit 123 or 224 in the above-described exemplary embodiment may include one or more function blocks. For example, the CRC decoder 424 and the error counter 425 illustrated in the exemplary embodiment of FIG. 4A may be function blocks included in the error detection units 123, 224 in the above-described exemplary embodiment of FIGS. 1 and 2.

The reception driver 421 receives the packet, including the data sequence, through the main link. The protocol decoder 422 decodes the packet according to a predetermined protocol to extract information included in the packet. For example, the display data DSP Data included in the packet may be provided to the data storage unit 423 and the CRC decoder 424. The received packet is data for a normal display operation, and the panel may be driven according to the display data DSP Data extracted from the packet to thereby output a screen.

During the normal display operation, the CRC decoder 424 calculates CRC data by using the display data DSP Data. For example, the CRC decoder 424 may output, as CRC data, a result obtained through a computation operation on the display data DSP Data. Whether an operation of the CRC decoder 424 is enabled may be controlled according to the error detection enabling information CRC EN. For example, a CRC decoding operation may be enabled according to a decoding result from the protocol decoder 422.

The error counter 425 may detect a bit error on the display data DSP Data transmitted through the main link and perform an operation of counting the number of errors. For example, the error counter 425 may receive the CRC data CRC Data (e.g., first CRC data) included in the packet from the protocol decoder 422 and receive the CRC data (e.g., second CRC data) calculated by the CRC decoder 424. The error counter 425 may compare whether the first CRC data is the same as the second CRC data, determine an error occurrence according to the comparison result, and count the number of errors when the errors occur.

As shown in FIG. 4B, the error counter 425 may include a comparator 425_1, a counting unit 425_2, and a register unit 425_3. The comparator 425_1 receives first CRC data CRC_ex from the protocol decoder 422, receives second CRC data CRC_cal from the CRC decoder 424, and outputs a comparison result of the first CRC data CRC_ex and the second CRC data CRC_cal. For example, when the first CRC data CRC_ex is the same as the second CRC data CRC_cal, the comparator 425_1 may output a comparison result of a first level, and when the first CRC data CRC_ex differs from the second CRC data CRC_cal, the comparator 425_1 may output a comparison result of a second level.

The counting unit 425_2 may detect the number of errors by counting comparison results from the comparator 425_1. For example, the counting unit 425_2 may detect the number of errors by counting a counting operation whenever a comparison result of the second level is received from the comparator 425_1. The counting unit 425_2 may be reset every predetermined period. For example, when an error detection operation on display data provided to pixels connected to one gate line is performed, the counting unit 425_2 may be reset whenever a test on one gate line is performed. Alternatively, when an error detection operation on display data of one frame is performed, the counting unit 425_2 may be reset whenever a test on all the gate lines is performed. The counting result may be stored in the register unit 425_3, and the counting result stored in the register unit 425_3 may be provided to the outside as a test result in response to a request from the outside.

Figure 6:
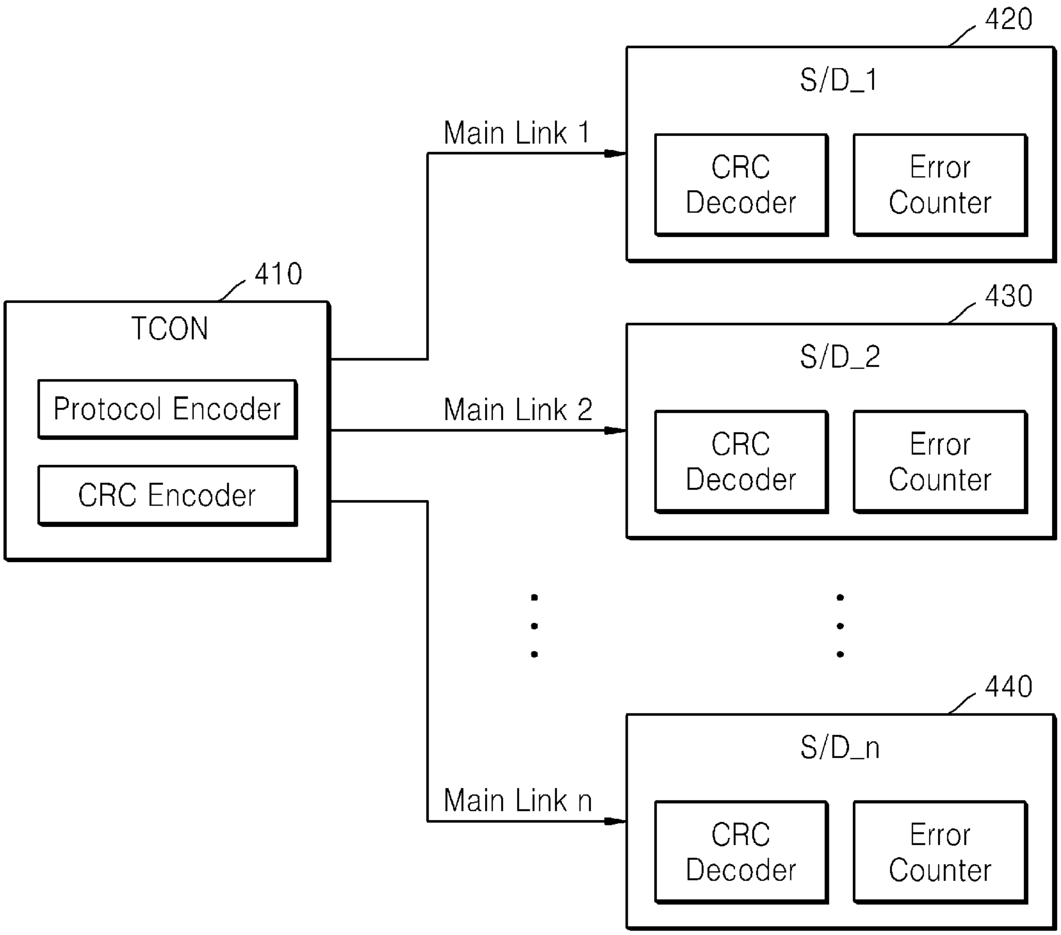
FIG. 6 is a block diagram for describing a test operation by a plurality of source drivers, according to an exemplary embodiment of the inventive concept.

FIG. 6 is a block diagram for describing a test operation by a plurality of S/Ds, according to an exemplary embodiment of the inventive concept. As shown in FIG. 6, a TCON 410 may communicate with a plurality of S/Ds S/D_1, S/D_2, . . . S/Dn (i.e., first to nth S/Ds 420 to 440) through main links Main Link 1, Main Link 2, . . . Main Link n (i.e., Main Link 1 to Main Link n) of the plurality of S/Ds, respectively. As described above, the TCON 410 may include a protocol encoder and a CRC encoder, and may simultaneously transmit a packet to each of the first to nth S/Ds 420 to 440. Since each of the first to nth S/Ds 420 to 440 drives a different data line of a panel, pieces of display data provided to the first to nth S/Ds 420 to 440 may be different from each other.

In addition, as described above, each of the first to nth S/Ds 420 to 440 may include an error detection unit. As function blocks included in the error detection unit, a CRC decoder and an error counter may be included in each of the first to nth S/Ds 420 to 440. Each of the first to nth S/Ds 420 to 440 performs an error counting operation through the CRC decoder for calculating CRC data from corresponding display data and the error counter for comparing CRC data included in a data sequence with the CRC data calculated by the CRC decoder. Each of the first to nth S/Ds 420 to 440 may store an error counting result, and each stored counting result may be provided to the TCON 410 as a test result. Test results from the first to nth S/Ds 420 to 440 may be simultaneously provided to the TCON 410.

Figure 7:
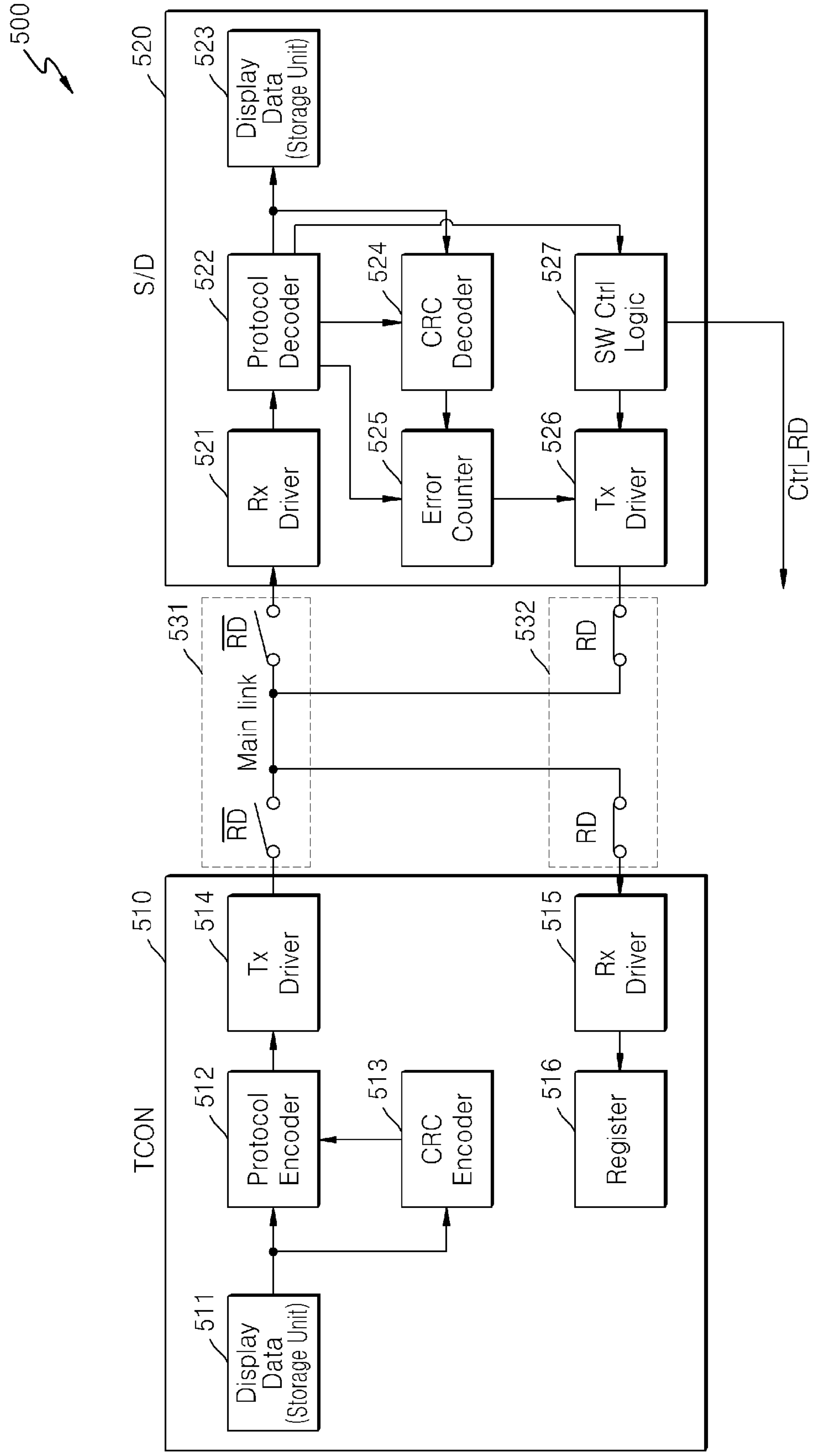
FIG. 7 is a block diagram of a DDI according to another exemplary embodiment of the inventive concept.

FIG. 7 is a block diagram of a DDI 500 according to another exemplary embodiment of the inventive concept. As shown in FIG. 7, the DDI 500 may include a TCON 510 and an S/D 520. The TCON 510 may include a storage unit 511 for temporarily storing display data, a protocol encoder 512 for converting data according to a transmission protocol, a transmission driver 514 for transmitting a packet including a data sequence, and a CRC encoder 513 for generating an error detection code from the display data. In addition, according to the current exemplary embodiment, the TCON 510 may further include an information reception unit (Rx Driver) 515 and a register 516. When an operation of the TCON 510 shown in FIG. 7 is described, the same components as described with reference to FIG. 4A perform substantially the same operations as described with reference to FIG. 4A, and thus, a detailed description thereof is omitted.

The TCON 510 and the S/D 520 may communicate through a main link. The main link may have a bidirectional transmission characteristic. For example, the TCON 510 may transmit a packet, including a data sequence, to the S/D 520, and the S/D 520 may transmit a test result to the TCON 510. For a bidirectional transmission control, one or more switches, namely, first and second switch units 531, 532, may be further included in the DDI 500.

Although FIG. 7 shows that the one or more switches, namely, the first and second switch units 531, 532, being arranged between the TCON 510 and the S/D 520, one or more exemplary embodiments of the inventive concept are not limited thereto. For example, the one or more switches, namely, the first and second switch units 531, 532, may be included in the TCON 510 or the S/D 520. Alternatively, only a portion of the one or more switches, namely, the first and second switch units 531, 532, may be included in the TCON 510 or the S/D 520.

A transmission mode is changed according to a connection state of the first and second switch units 531, 532. For example, when the first switch unit 531 is turned on, a transmission direction of the main link is determined according to a first transmission mode, and the TCON 510 transmits a packet to the S/D 520 in the first transmission mode. When the second switch unit 532 is turned on, a transmission direction of the main link is determined according to a second transmission mode, and the S/D 520 transmits a test result to the TCON 510 in the second transmission mode.

The information reception unit 515 receives a test result from the S/D 520 in the second transmission mode. As described in the above-described exemplary embodiment, the test result may be a counting result stored in a register of the S/D 520. The received test result may be stored in the register 516 included in the TCON 510.

The S/D 520 may include a reception driver 521, a protocol decoder 522, a data storage unit 523, a CRC decoder 524, and an error counter 525. In addition, according to the current embodiment, the S/D 520 may further include a test result transmission unit (Tx Driver) 526 and a switch control logic 527. When an operation of the S/D 520 shown in FIG. 7 is described, the same components as described with reference to FIG. 4A perform substantially the same operations as described with reference to FIG. 4A, and thus, a detailed description thereof is omitted.

According to a decoding operation of the protocol decoder 522, whether information for requesting to transmit an error counting result is enabled may be determined. For example, if error detection request information is enabled as in the above-described embodiment, the CRC decoder 524 and the error counter 525 may operate to perform an error detection operation on display data. On the contrary, if error detection request information is disabled and information for requesting to transmit an error counting result is enabled, a counting result stored in the register included in the S/D 520 may be provided to the TCON 510. In this case, under control of the protocol decoder 522, the counting result stored in the register is provided to the test result transmission unit 526, and the test result transmission unit 526 transmits the counting result as a test result to the TCON 510 through the main link.

In addition, when the test result is transmitted, the switch control logic 527 generates and outputs a switch control signal Ctrl_RD to change the transmission mode of the main link. The switch control logic 527 may generate the switch control signal Ctrl_RD under control of the protocol decoder 522. In response to the switch control signal Ctrl_RD, the first switch unit 531 may be turned off, and the second switch unit 532 may be turned on.

A test result operation may be performed during a vertical blank period (VBP) in association with display timing. For example, in the VBP, the TCON 510 may provide information for requesting to transmit an error counting result to the S/D 520, and the S/D 520 may change the transmission mode between the TCON 510 and the S/D 520 through a protocol decoding operation. A test result is provided to the TCON 510 through the main link, and when the test result is completely transmitted, the transmission mode between the TCON 510 and the S/D 520 is changed again, thereby performing a normal operation (e.g., a normal display operation). As in the above-described embodiment, a normal display operation and a test result transmission operation may be simultaneously performed.

Figure 8A:
FIGS. 8A and 8B are respectively a data format of a packet according to the embodiment of FIG. 7 and a block diagram for describing a switch control operation according to another exemplary embodiment of the inventive concept.
Figure 8B:
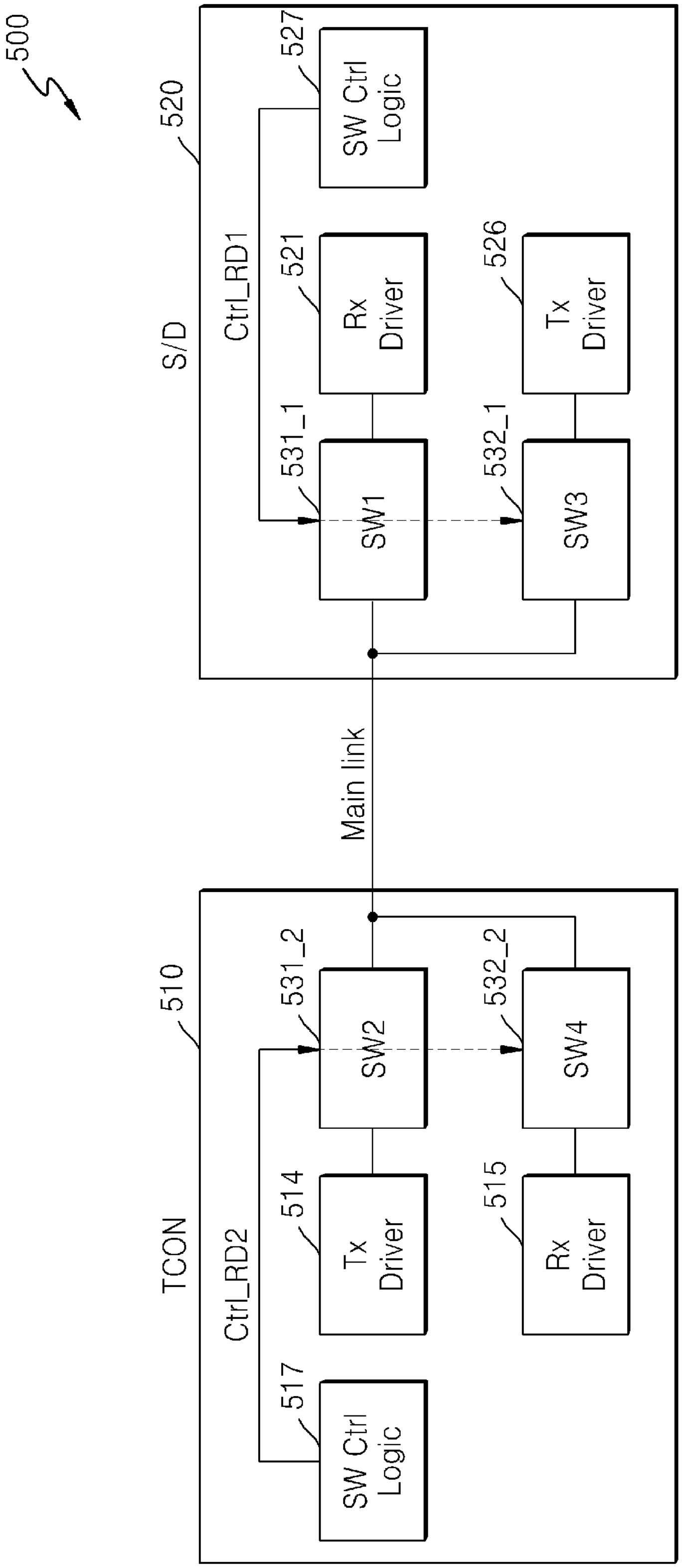

FIGS. 8A and 8B depict a data format of a packet according to the embodiment of FIG. 7 and a block diagram for describing a switch control operation according to another exemplary embodiment of the inventive concept, respectively. As shown in FIG. 8A, a packet including a data sequence may include display data DSP Data and one or more pieces of information SOL and HBP. In addition, error detection request information CRC En may be enabled so as to provide an error detection request together with a normal display operation in the first transmission mode, or test result request information RD En may be enabled so as to provide an error counting result transmission request in the second transmission mode. Since each of the above-described operations may be exclusively performed, any one of the error detection request information CRC En and the test result request information RD may be selectively enabled.

As shown in FIG. 8B, at least one switch may be arranged inside the TCON 510 and/or the S/D 520. In addition, a switch control logic may be included in the TCON 510 and/or the S/D 520. For example, to operate the main link according to the first transmission mode, a first switch SW1 531_1 may be arranged inside the S/D 520, and a second switch SW2 531_2 may be arranged inside the TCON 510. In addition, to operate the main link according to the second transmission mode, a third switch SW3 532_1 may be arranged inside the S/D 520, and a fourth switch SW4 532_2 may be arranged inside the TCON 510.

During a normal display operation, a data sequence, including display data and CRC data, is provided to the S/D 520 through the main link, and a switch control logic 517 outputs a switch control signal Ctrl_RD2 so as to turn the second switch SW2 531_2 on and to turn the fourth switch SW4 532_2 off. In addition, during the normal display operation, the first switch SW1 531_1 maintains a turn-on state, and the third switch SW3 532_1 maintains a turn-off state.

Thereafter, when a test result transmission is requested, the TCON 510 enables test result request information and outputs the test result request information through the second switch SW2 531_2, and the switch control logic 517 outputs the switch control signal Ctrl_RD2 so as to turn the second switch SW2 531_2 off and to turn the fourth switch SW4 532_2 on. The switch control logic 527 in the S/D 520 turns the first switch SW1 531_1 off and the third switch SW3 532_1 on in response to the test result request information. Accordingly, the main link operates in the second transmission mode, and thus, a test result from the S/D 520 is provided to the TCON 510 through the main link.

Figure 9:
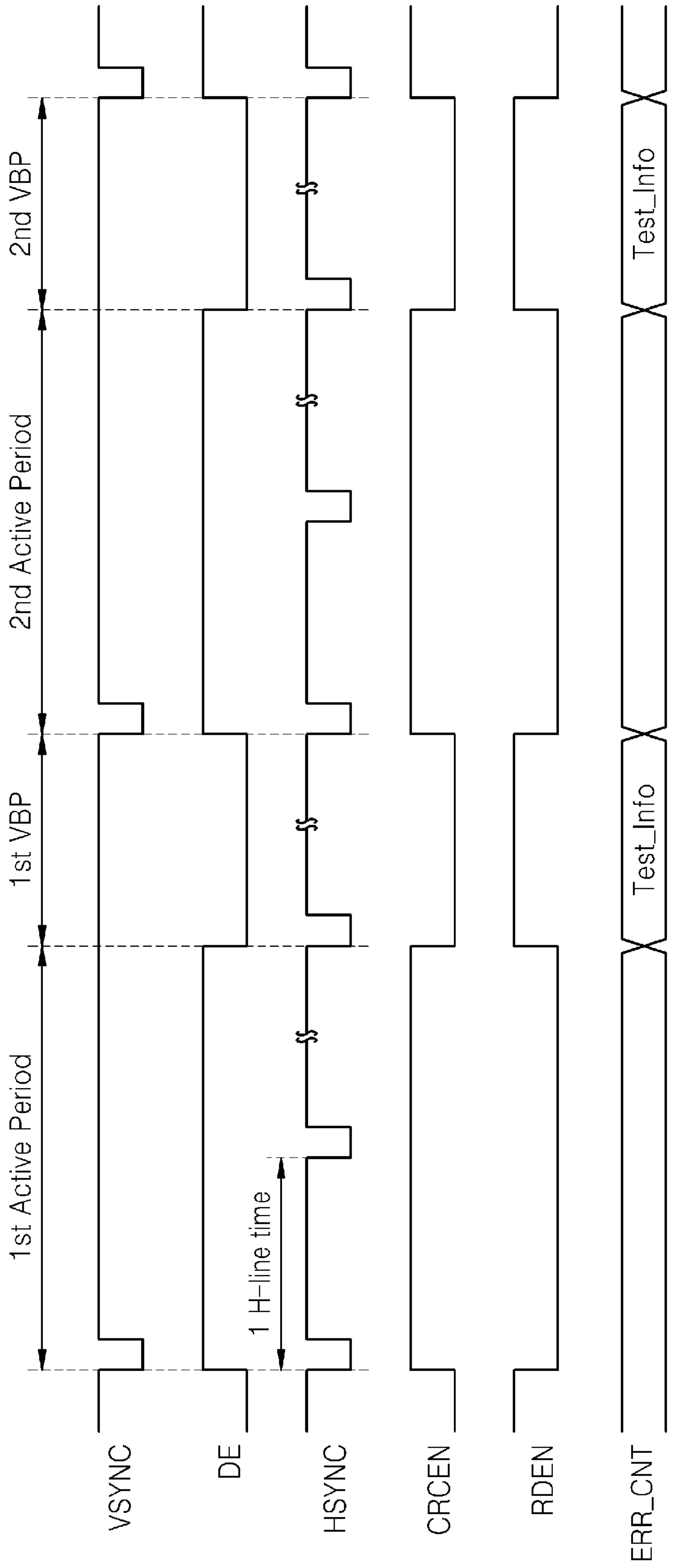
FIG. 9 is a waveform diagram for describing an error detection operation and a test result transmission operation, according to an exemplary embodiment of the inventive concept.

FIG. 9 is a waveform diagram for describing an error detection operation and a test result transmission operation, according to an exemplary embodiment of the inventive concept.

As shown in FIG. 9, various kinds of timing signals for a normal display operation may be provided from a TCON to a G/D and an S/D. For example, a vertical synchronization signal VSYNC having a period corresponding to an output period with respect to one frame and a horizontal synchronization signal HSYNC having a period corresponding to a driving period with respect to one gate line may be output from the TCON. In addition, a data enable signal DE indicating a display data providing period may be output from the TCON. In addition, as described in the above-described embodiment, error detection enabling information CRC_EN and/or test result request information RD_EN may be enabled. The error detection enabling information CRC_EN and the test result request information RD_EN may be selectively enabled.

A VBP may be between active periods in which an image is output by a panel according to display data. During the VBP, data may not be transmitted between the TCON and the S/D, and accordingly, a main link is set as the second transmission mode, and one or more pieces of information may be provided from the S/D to the TCON through the main link. As in the above-described embodiment, the number of error bits while driving pixels located on each gate line of the panel and a result of counting the number of error bits with respect to all the gate lines may be calculated. The calculated error counting result may be temporarily stored in a register in the S/D. When the test result request information RD_EN is enabled, the S/D may transmit the error counting result as a test result to the TCON during the VBP.

Figure 10:
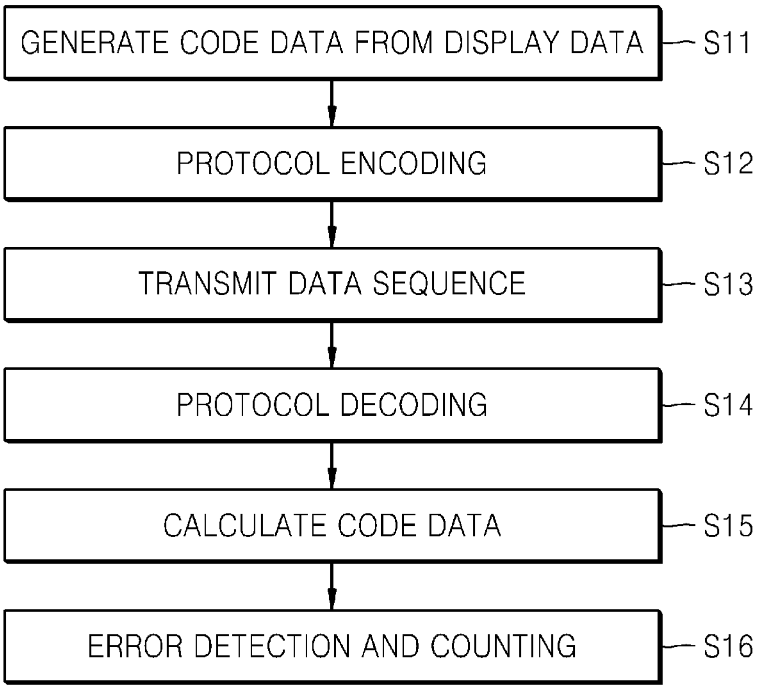
FIG. 10 is a flowchart of a method of operating a DDI, according to an exemplary embodiment of the inventive concept.

FIG. 10 is a flowchart of a method of operating a DDI, according to an exemplary embodiment of the inventive concept.

As shown in FIG. 10, code data for error detection is generated (step S11) from display data during a normal display operation. As in the above-described embodiment, the code data may be any one of various kinds of code data used for error detection and correction. The code data may be, for example, CRC data.

Protocol encoding is performed (step S12) to transmit information according to a pre-defined protocol between a TCON and an S/D (or the DDI). A packet, including a data sequence, is generated according to the protocol encoding operation, wherein the data sequence may include display data and the code data. In addition, the data sequence may further include one or more pieces of information. For example, information for requesting for an error detection operation on the display data may be enabled and included in the data sequence. The packet, including the data sequence, is transmitted (step S13) to the S/D through a main link.

The S/D performs a protocol decoding operation (step S14) on the received packet. According to a protocol decoding result, an error detection operation may be enabled. When the error detection operation is enabled, code data is calculated (step S15) through a decoding operation on the display data. The error detection operation is performed by using the code data included in the received packet and the code data calculated through the decoding operation. A test on display data transmission through links is performed (step S16) by counting the number of errors.

Figure 11:
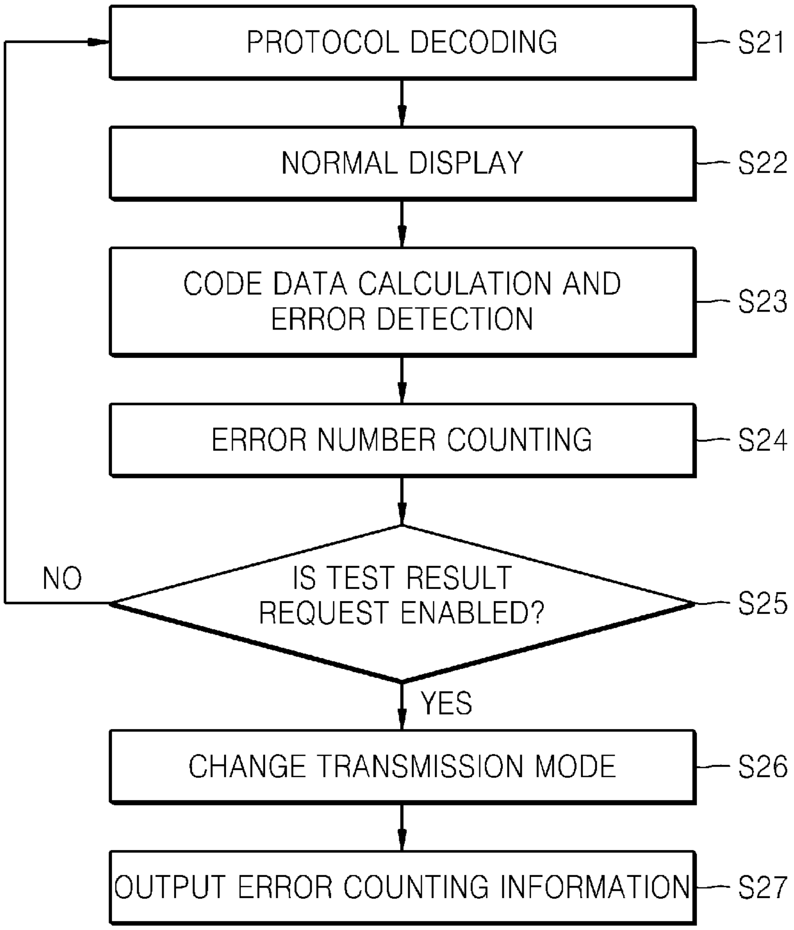
FIG. 11 is a flowchart of a method of operating a DDI, according to another exemplary embodiment of the inventive concept.

FIG. 11 is a flowchart of a method of operating a DDI, according to another exemplary embodiment of the inventive concept. FIG. 11 illustrates an operating method related to the transmission of a test result.

When a data sequence, including display data and code data, is provided to an S/D, a protocol decoding operation is performed (step S21). The data sequence may include one or more pieces of information, and, for example, error detection request information may be enabled.

As the error detection request information is enabled, a normal display operation is performed (step S22) using the received display data, and code data is calculated from the display data for a link test operation. An error detection operation is performed (step S23) by comparing the calculated code data with the code data included in the data sequence. The number of errors is counted (step S24) according to a result of the error detection operation. The error counting information may be stored as a test result in a register included in the S/D.

Thereafter, a data sequence may be provided from a TCON to the S/D, and test result request information may be enabled and included in the data sequence. Whether the test result request information is enabled is determined (step S25) through a protocol decoding operation. If the test result request information is disabled and the error detection request information is maintained enabled, the above-described normal display and error detection operations are performed. On the other hand, if the test result request information is enabled, a transmission mode of a link is changed (step S26), and the error counting information stored in the S/D is output (step S27) as a test result to the TCON.

Figure 12:
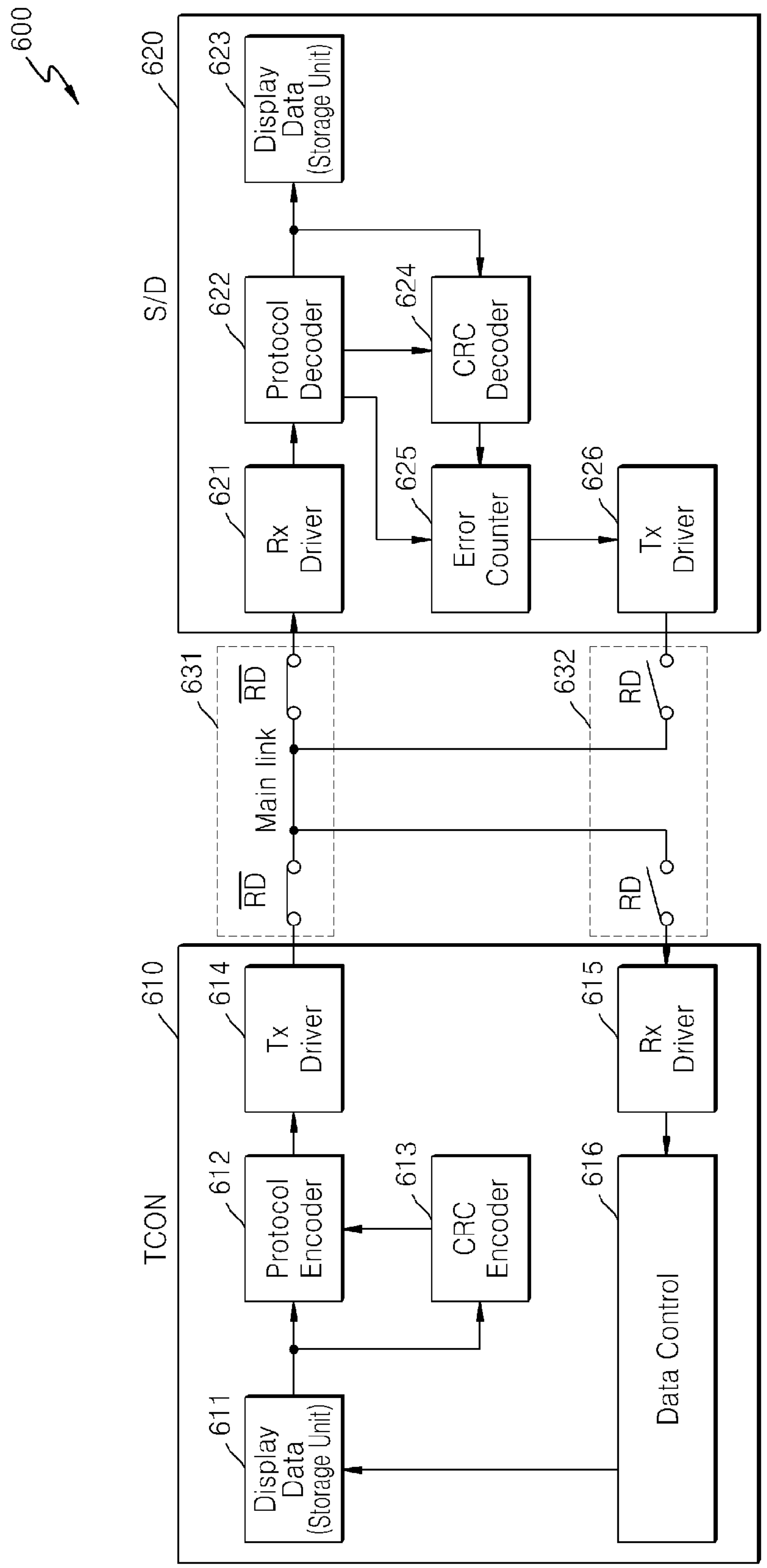
FIG. 12 is a block diagram of a DDI according to another exemplary embodiment of the inventive concept.

FIG. 12 is a block diagram of a DDI 600 according to another exemplary embodiment of the inventive concept. As shown in FIG. 12, the DDI 600 may include a ICON 610 and an S/D 620. The TCON 610 may include a storage unit 611 for temporarily storing display data, a protocol encoder 612 for converting data according to a transmission protocol, a transmission driver 614 for transmitting a packet including a data sequence, and a CRC encoder 613 for generating an error detection code from the display data. In addition, according to the current embodiment, the TCON 610 may further include an information reception unit (Rx Driver) 615 and a data control unit 616. The data control unit 616 may further include a register. Alternatively, although not shown in FIG. 12, the register may be arranged outside the data control unit 616.

The S/D 620 may include a reception driver 621, a protocol decoder 622, a data storage unit 623, a CRC decoder 624, an error counter 625, and a transmission driver 626. Although not shown in FIG. 12, at least one of the TCON 610 and the S/D 620 may include a switch control logic for controlling switches 631, 632. When an operation of the TCON 610 and the S/D 620 shown in FIG. 12 is described, the same components as described with reference to FIGS. 4A and 7 perform substantially the same operations as described with reference to FIGS. 4A and 7, and thus, a detailed description thereof is omitted.

The information reception unit 615 receives a test result from the S/D 620. The received test result is provided to the data control unit 616. The TCON 610 may simultaneously receive test results from a plurality of S/Ds 620, and the received test results may be stored in a storage unit (e.g., a register) included in the data control unit 616.

The data control unit 616 displays the test result on a panel (not shown) of a display apparatus through a data control operation. For example, when a test result transmission mode ends, a normal display mode is performed again, and the test result may be displayed on the panel during a normal display operation. The data control unit 616 controls a combination of test data, which corresponds to the test result, and display data.

Together with the display of the test result, the error detection operation as in the above-described embodiment may be performed according to the normal display operation. The CRC encoder 613 may generate CRC data from the display data and output the generated CRC data to the protocol encoder 612. According to an exemplary embodiment of the inventive concept, the CRC encoder 613 may generate the CRC data by computing the display data or by computing data in which the display data and the test data are combined. A data sequence, including the display data and the CRC data, may be transmitted to the S/D 620 through a main link.

Figure 14A:
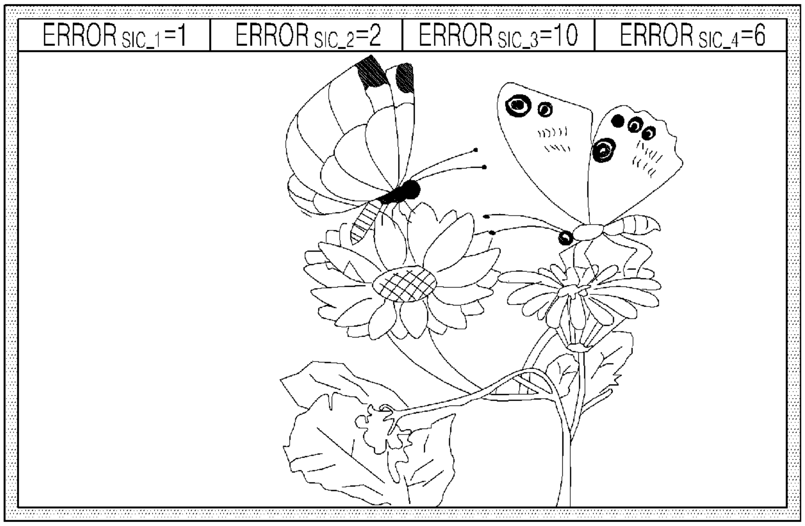
FIGS. 14A, 14B, and 14C illustrate output screens of display data and test data.
Figure 14B:
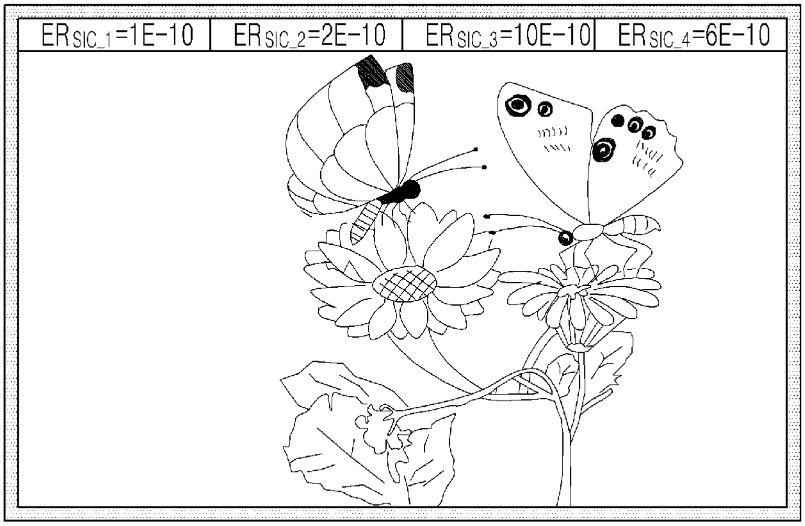
Figure 14C:
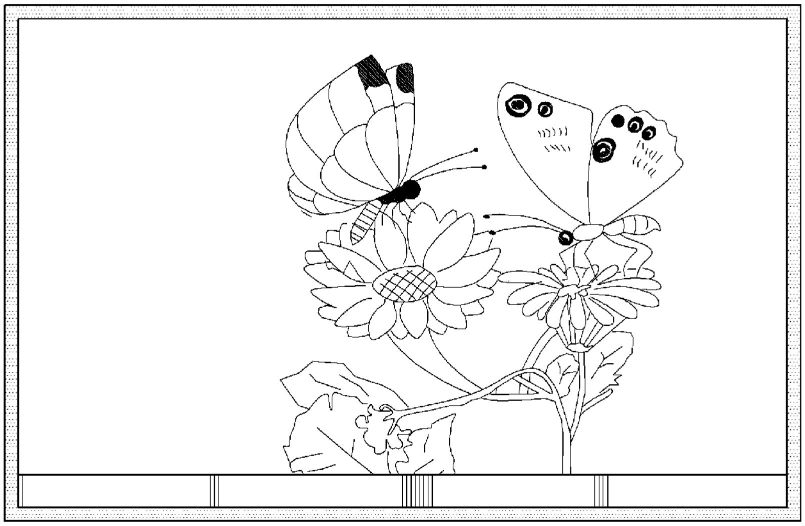

Test result output screens according to the embodiment of FIG. 12 will now be described with reference to FIGS. 14A, 14B, and 14C. FIGS. 14A, 14B, and 14C illustrate output screens of display data and test data.

As shown in FIGS. 14A, 14B, and 14C, together with an output of a screen to a panel according to a normal display operation, a test result is displayed on at least a portion of the screen according to test data included in a data sequence. FIG. 14A shows an example in which test results according to corresponding S/Ds are displayed on the top of a screen. When the panel is driven by first to fourth S/Ds, the test results of the first to fourth S/Ds may be displayed on the screen. Each test result may be displayed as the number of error bits generated with respect to one frame. For example, FIG. 14A shows that the first S/D has detected one bit error, the second S/D has detected two bit errors, the third S/D has detected ten bit errors, and the fourth S/D has detected six bit errors.

FIG. 14B shows an example in which an error rate for each S/D is displayed as text, wherein an error counting result is converted into an error rate, and an error rate of each S/D is qualified and displayed on the top of a screen. FIG. 14C shows an example in which an error counting result is displayed in a bar form on the bottom of a screen.

Referring back to FIG. 12, during a VBP, error counting information may be accessed by the S/D 620 and provided to the TCON 610. When the plurality of S/Ds 620 are provided, each S/D 620 may operate a portion of the panel, and information obtained by counting the number of error bits of data processed by each S/D 620 may be provided to the TCON 610. The TCON 610 may provide test data according to test results with respect to a previous frame together with display data for displaying a current frame when the display data for displaying the current frame is provided so that the test results are displayed in real-time. In addition, by reflecting test results with respect to the current frame in display data of a subsequent frame, test results by the plurality of S/Ds 620 are continuously displayed in real-time.

Figure 13:
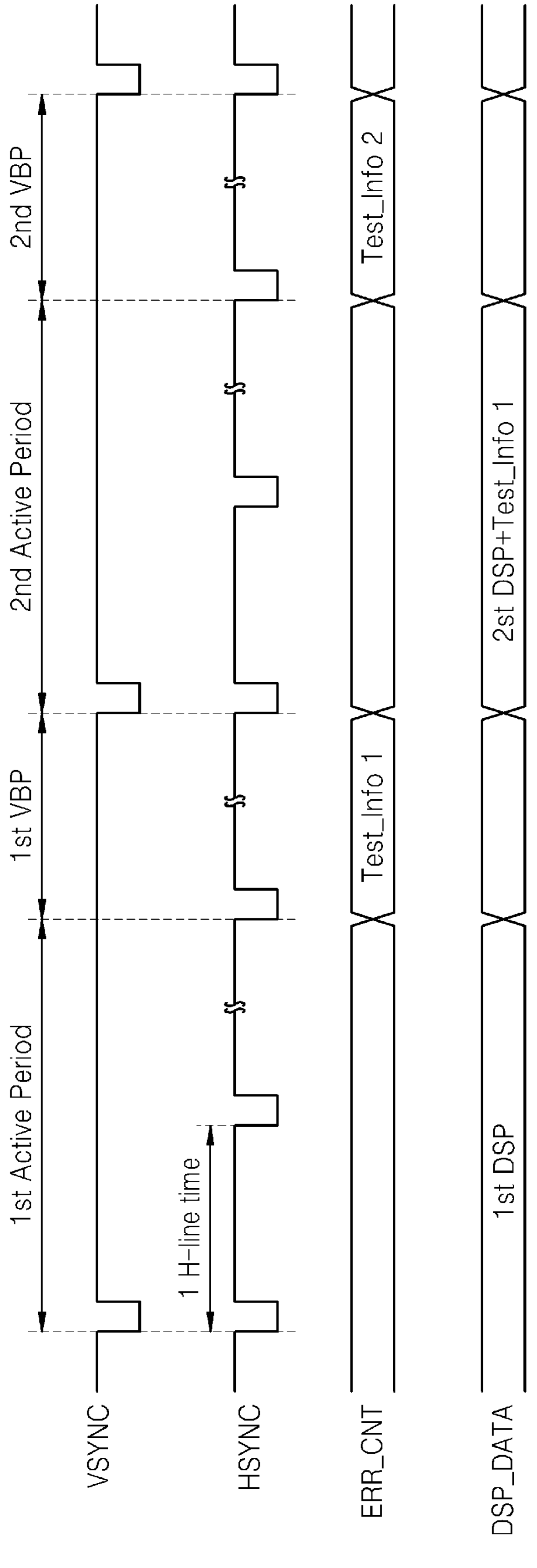
FIG. 13 is a waveform diagram for describing an operation of the DDI of FIG. 12.

FIG. 13 is a waveform diagram for describing an operation of the DDI 600 of FIG. 12. FIG. 13 shows an example of a test result output operation by the TCON 610.

As shown in FIG. 13, when a vertical synchronization signal VSYNC is enabled, a horizontal synchronization signal HSYNC is simultaneously enabled in correspondence with each gate line. First display data $1^{st}$ DSP related to a first frame is provided to the S/D 620, and an error counting operation on pixels connected to each gate line is performed. As in the above-described embodiment, an error counting result for pixels connected to a plurality of gate lines with respect to one frame is calculated and stored.

After a first active period, according to a request of the TCON 610, a first test result Test Info 1 may be provided from the S/D 620 to the TCON 610 during a first VBP. When the TCON 610 provides data to be output during a second active period, the TCON 610 may combine display data corresponding to a screen that is to be normally output during the second active period (e.g., second display data $2^{nd}$ DSP) and test data to which the first test result Test Info 1 is reflected, and then the TCON 610 may provide the combined data to the S/D 620. According to the combined data, the first test result Test Info 1 may be displayed on the screen in various forms. For example, the normal screen according to the second display data $2^{nd}$ DSP may be output at a portion of the panel, and a test result screen according to the test data corresponding to the first test result Test Info 1 may be output at the other portion of the panel.

Figure 15A:
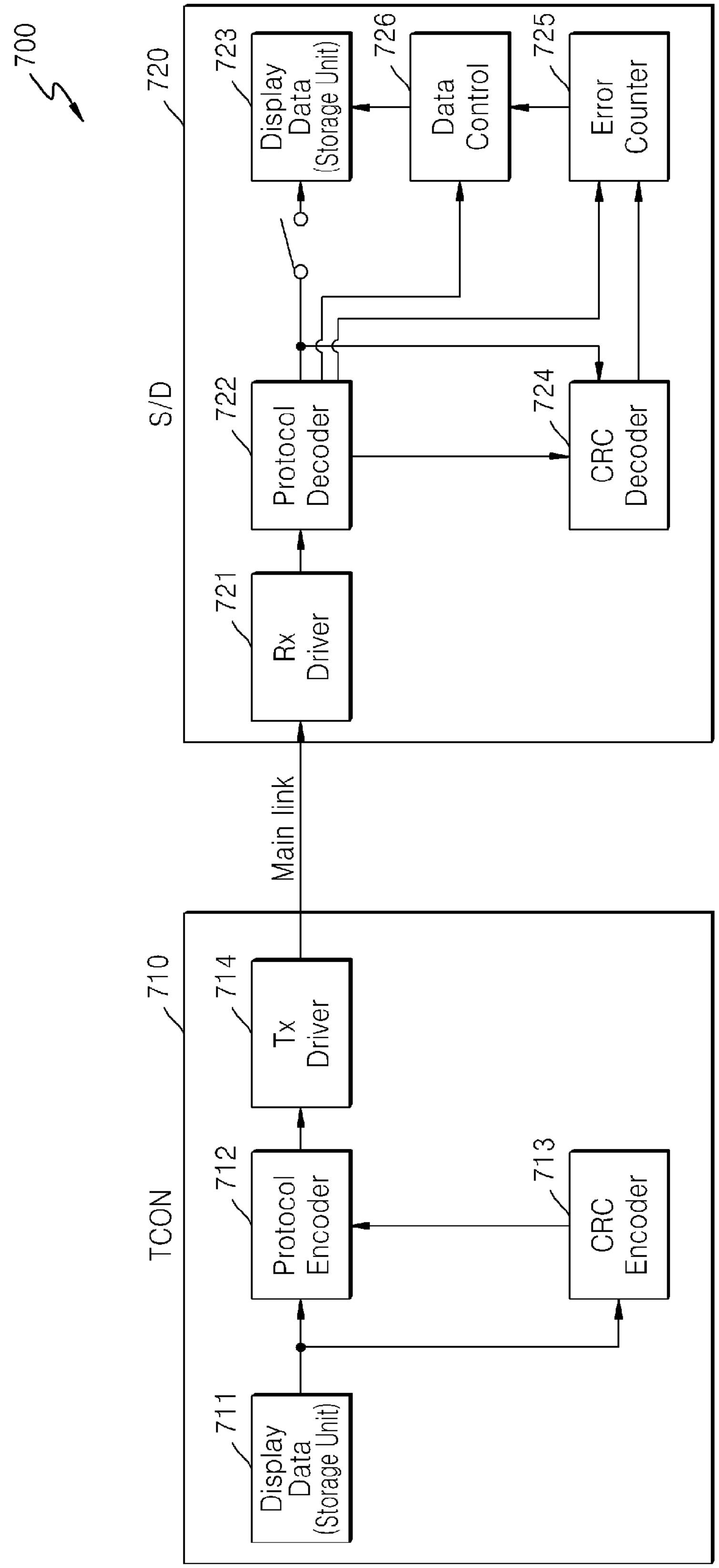
FIGS. 15A and 15B are respectively a block diagram of a DDI and a data format of a packet according to another exemplary embodiment of the inventive concept.
Figure 15B:

FIGS. 15A and 15B depict a block diagram of a DDI 700 and a data format of a packet according to another exemplary embodiment of the inventive concept, respectively. As shown in FIG. 15A, the DDI 700 may include a TCON 710 and an S/D 720. The TCON 710 may include a storage unit 711 for temporarily storing display data, a protocol encoder 712 for converting data according to a transmission protocol, a transmission driver 714 for transmitting a packet including a data sequence, and a CRC encoder 713 for generating an error detection code from the display data. In addition, the S/D 720 may include a reception driver 721, a protocol decoder 722, a data storage unit 723, a CRC decoder 724, an error counter 725, and a data control unit 726. Some of the function blocks illustrated in the embodiments described above are not shown in FIG. 15A for convenience of description. Other function blocks may be further included in the DDI 700 of FIG. 15A. When an operation of the TCON 710 and the S/D 720 shown in FIG. 15 is described, the same components as described with reference to FIGS. 4A, 7, and 12 perform substantially the same operations as described with reference to FIGS. 4A, 7, and 12, and thus, a detailed description thereof is omitted.

When the TCON 710 provides display data and CRC data to the S/D 720, the TCON 710 may enable first information CRC En for requesting to perform an error detection operation and provide the first information CRC En to the S/D 720. In addition, the TCON 710 may enable result output information (e.g., second information VCRC En) for outputting a test result according to an error detection operation to a panel and provide the second information VCRC En to the S/D 720. According to a decoding operation of the protocol decoder 722, the S/D 720 may perform an error detection operation on the display data and may also perform an operation of outputting an error detection result (or a test result).

An error counting result from the error counter 725 is provided to the data control unit 726. In addition, according to the enabling of the second information VCRC En, the data control unit 726 may perform a data combination operation for a test output operation. For example, the data control unit 726 may reflect the error counting result to the display data temporarily stored in the data storage unit 723. Accordingly, during a normal display operation, the test result is output in real-time.

As another example, when the second information VCRC En is enabled, the data control unit 726 may perform a control operation so as to output the test result regardless of the display data provided from the TCON 710. For example, information (display data information) related to a screen on which the test result is displayed may be pre-defined and set in the data control unit 726, and the pre-set information and the test result may be combined and displayed on a screen.

Figure 16A:
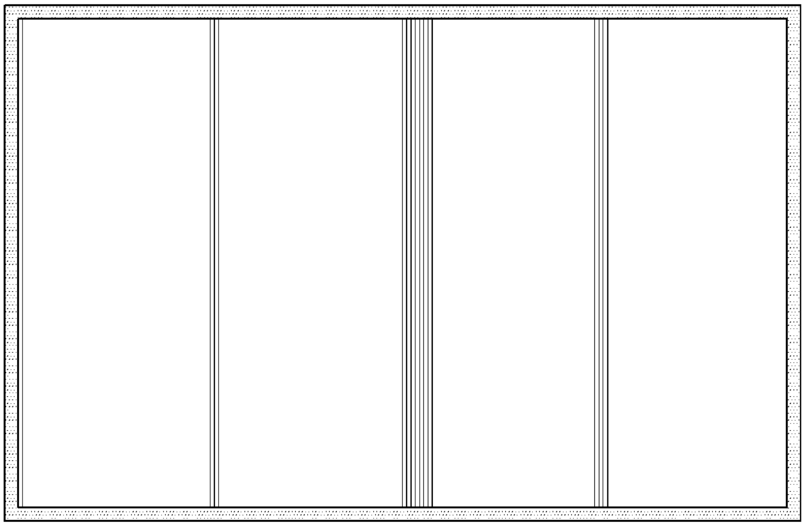
FIGS. 16A and 16B illustrate output screens of test results according to the DDI of FIG. 15A.
Figure 16B:
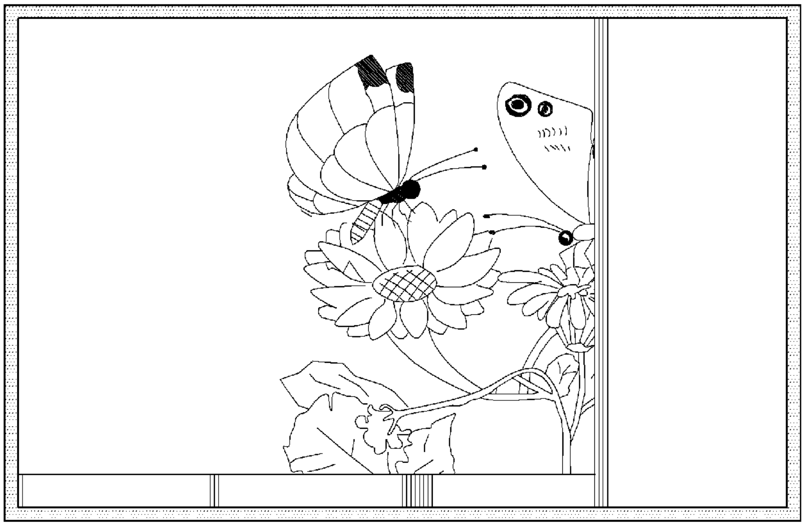

FIGS. 16A and 16B illustrate output screens of test results according to the DDI 700 of FIG. 15A. FIG. 16A shows an example in which test results are displayed on the entire screen. When the second information VCRC En is enabled, the data control unit 726 stops outputting on a screen according to display data temporarily stored in the data storage unit 723 and controls so that a test result is output for each S/D 720 through data conversion. FIG. 16B shows an example in which some S/Ds 720 drive data such that only test results are output, and the other S/Ds 720 drive data such that a normal display operation and a test result output operation are simultaneously performed. For example, first to third S/Ds 720 simultaneously perform a normal display operation and a test result output operation through a data combination operation. However, a fourth S/D 720 outputs a test result in a bar form without performing a normal display operation through a data conversion operation.

According to embodiments, test results may be output in various forms. For example, an error counting result for a current frame may be displayed on a portion of a screen (e.g., on the bottom of the screen) of the current frame or displayed on a portion of a screen (e.g., on the top of the screen) of a subsequent frame. Alternatively, when an error counting result for a current frame is calculated, for a subsequent frame, a normal display operation may be not performed, and a test result may be displayed on the entire screen in a predetermined form (e.g., a bar form).

A test result may be displayed substantially at the same time as a normal display operation. For example, a normal display operation and a test result output operation may be simultaneously performed by temporarily storing display data in the data storage unit 723 and combining the test result with the temporarily stored display data.

Figure 17:
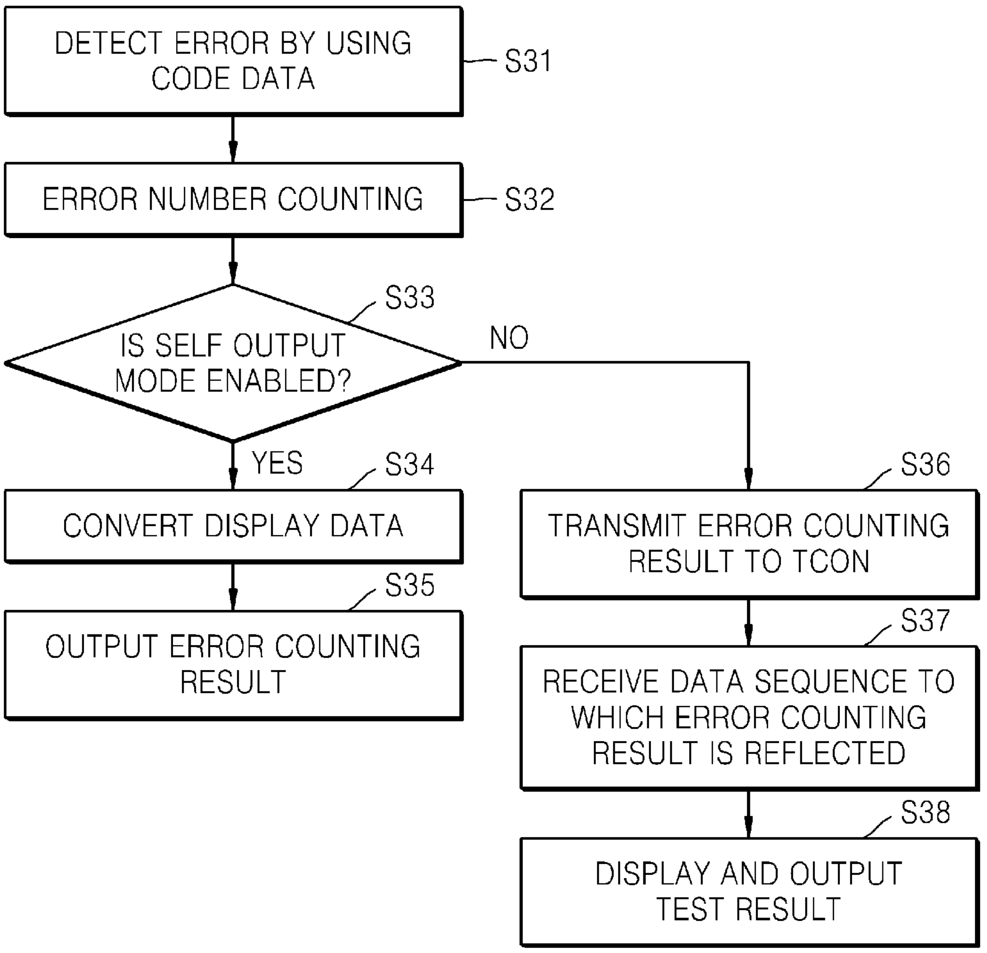
FIG. 17 is a flowchart of a method of operating a DDI, according to another exemplary embodiment of the inventive concept.

FIG. 17 is a flowchart of a method of operating a DDI, according to another exemplary embodiment of the inventive concept. FIG. 17 illustrates an operating method related to a test result output.

Code data corresponding to display data is generated by a TCON and provided to an S/D, and the S/D performs an error detection operation (step S31) using the code data. An error number counting operation according to an error detection result is performed (step S32), and whether a test result output mode through an operation of the S/D is enabled is determined (step S33). The determination operation may be performed according to whether predetermined information provided from the TCON to the S/D is enabled.

As a result of the determination, if the test result output mode through an operation of the S/D is enabled, the S/D converts (step S34) the display data. For example, the test data may be combined with the display data. An error counting result is output (step S35) by displaying the combined data on a panel.

Otherwise, if the test result output mode through an operation of the S/D is disabled, the test result may be output under control of the TCON. For example, the error counting result is transmitted (step S36) to the TCON. The TCON combines the test data according to the error counting result with subsequent display data, and transmits a data sequence to the S/D through a protocol encoding operation. The S/D receives (step S37) the data sequence to which the error counting result is reflected, and outputs the test result together with performing normal display (step S38) through a protocol decoding operation.

Figure 18A:
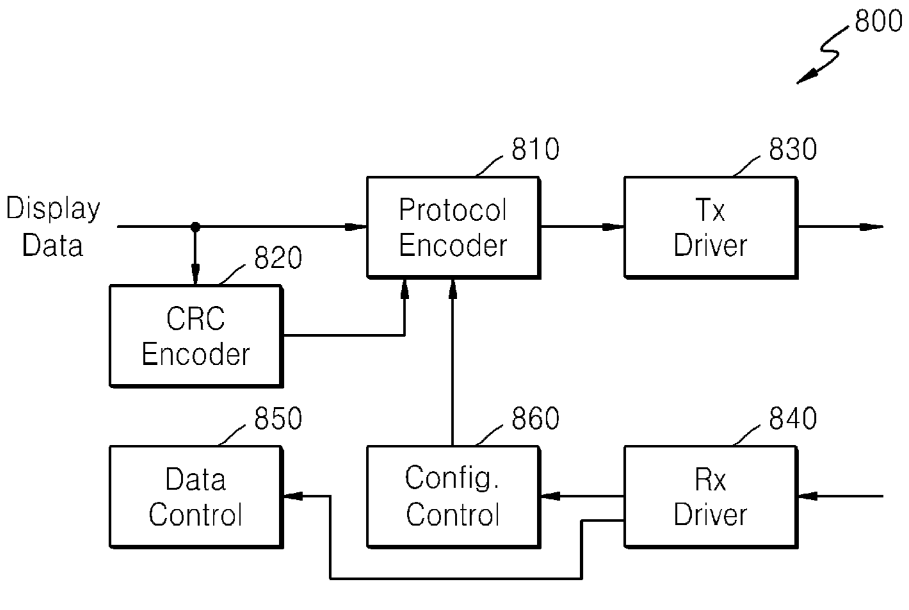
FIGS. 18A and 18B are a block diagram and a flowchart for describing an example in which an operation of a DDI is optimized according to a test result.
Figure 18B:
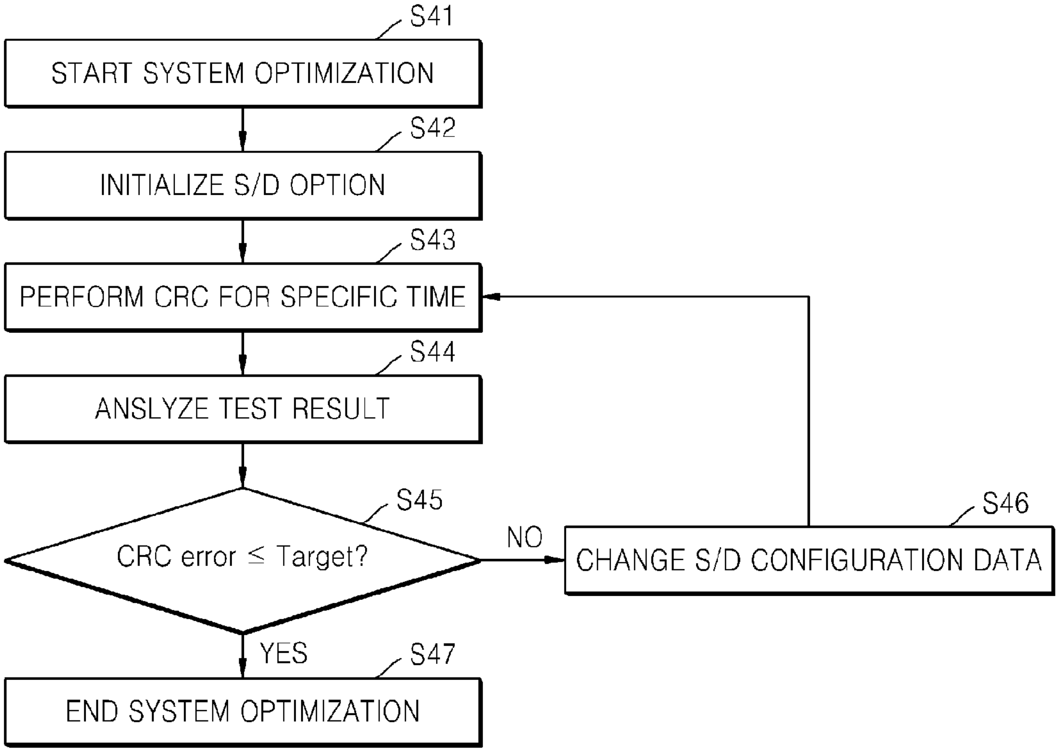

FIGS. 18A and 18B are a block diagram and a flowchart for describing an example in which an operation of a DDI is optimized according to a test result. FIG. 18A shows only a TCON 800 for convenience of description, respectively. When an operation of the TCON 800 shown in FIG. 18A is described, the same components as described with reference to FIG. 12 perform substantially the same operations as described with reference to FIG. 12, and thus, a detailed description thereof is omitted.

As shown in FIG. 18A, the TCON 800 may include a protocol encoder 810 for converting data according to a transmission protocol, a transmission driver 830 for transmitting a packet including a data sequence, and a CRC encoder 820 for generating an error detection code from the display data. In addition, according to the current embodiment, the TCON 800 may further include an information reception unit (Rx Driver) 840, a data control unit 850, and an environment configuration control unit 860 for setting an operational environment of the DDI (e.g., including a G/D and an S/D).

As in the embodiments described above, the data control unit 850 displays a test result on a panel (not shown) of a display apparatus through a data control operation. Besides, the DDI, including a G/D, an S/D, and the like, may not satisfy an error level desired by a system due to a change in an ambient environment (e.g., temperature rise, applied external noise, and the like) during normal display. In this case, the DDI may change the operational environment by changing environment configuration information (e.g., operational environment change such as adjustment of a level of a bias to a high level), and accordingly, a system may be optimized.

The system optimization operation as described above may be performed in various forms. For example, the environment configuration information may be directly changed by arranging means for storing the environment configuration information in the G/D or the S/D or may be changed by providing changed environment configuration information from the TCON 800 to the G/D or the S/D. According to one or more embodiments of the inventive concept, an environment configuration information change function as described above may be provided in various forms. As an example, the changed environment configuration information provided from the TCON 800 will now be described.

The environment configuration control unit 860 may receive a test result from the information reception unit 840 and determine whether the test result exceeds a preset target error rate. Environment configuration information that is changed according to the determination result may be provided to the protocol encoder 810. The environment configuration information is included in a packet, and provided to the S/D. The system optimization operation may be performed by periodically monitoring the test result or performed at an arbitrary time according to a request of the TCON 800 (or a host).

FIG. 18B illustrates an operating method related to the system optimization described above. When a system optimization operation starts (step S41), an option of an S/D is initialized (step S42) according to initially defined environment configuration information. In addition, according to the various embodiments described above, an error detection operation may be performed during normal display, and an error counting result may be provided as a test result to a TCON. For the system optimization, the error detection and test result transmission operation is performed (step S43) for a specific time. The error detection and test result transmission operation may be defined as a CRC operation for convenience of description.

The test result is analyzed (step S44) by the TCON. Operation S44 is only an example, and the TCON may receive the test result and transmit the test result to a host so that the host analyzes the test result. When it is assumed that the TCON analyzes the test result, it is determined (step S45) whether the error counting result is equal to or less than a target value. If the error counting result is equal to or less than the target value, it is determined that the system optimization is achieved according to current environment configuration information, and the system optimization operation is ended (step S47). Otherwise, if the error counting result is greater than the target value, the system optimization operation is performed by changing (step S46) environment configuration information of the S/D.

Figure 19:
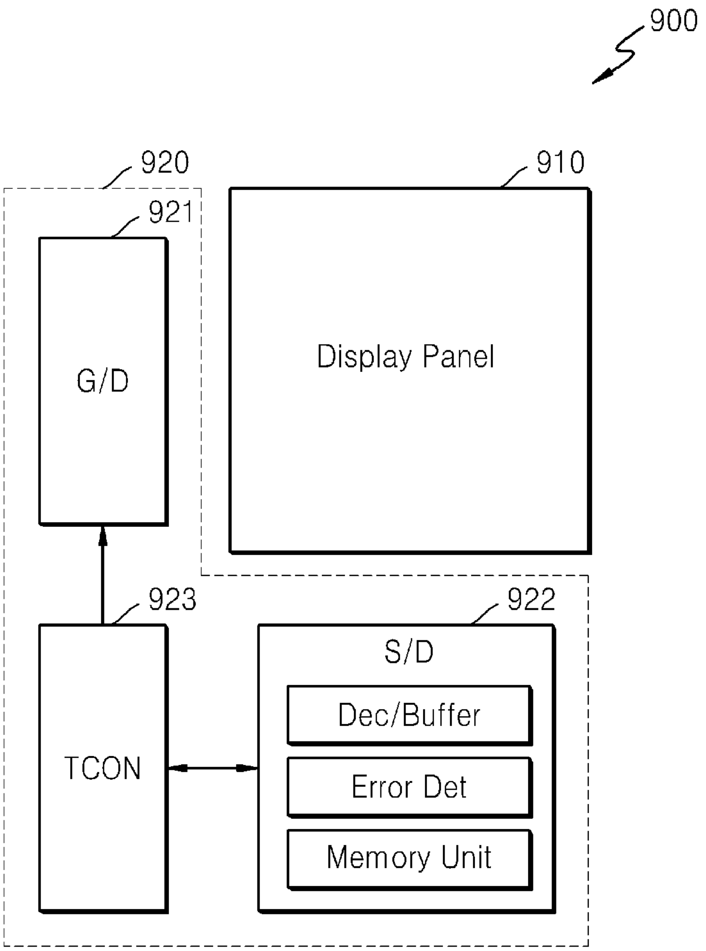
FIG. 19 is a block diagram of a display apparatus according to an exemplary embodiment of the inventive concept.

FIG. 19 is a block diagram of a display apparatus 900 according to an exemplary embodiment of the inventive concept. FIG. 19 shows an example in which a mobile-oriented DDI 920 is included in the display apparatus 900.

As shown in FIG. 19, the display apparatus 900 may include a display panel 910 and the DDI 920. The DDI 920 may include a G/D 921, an S/D 922, and a TCON 923. The G/D 921, the S/D 922, and the TCON 923 may be implemented as one semiconductor chip. The S/D 922 may include a memory unit for storing display data (e.g., frame data), an error detection unit for performing an error detection operation (e.g., including comparison and counting operations) according to one or more embodiments of the inventive concept, a decoder for generating an analog data signal, and a buffer unit for outputting a data signal to the display panel 910.

The TCON 923 and the S/D 922 may perform bidirectional communication through a main link. In addition, as in the above-described embodiments, the TCON 923 may generate code data from display data and provide a data sequence, including the display data and the code data, to the S/D 922. One or more S/Ds 922 may be included in the DDI 920, and in this case, a data sequence may be transmitted to each S/D 922 through different main links. The S/D 922 may perform an error detection operation using the received code data and provide an error counting result to the TCON 923 through the main link. In addition, as in the above-described embodiments, when a test result is output, the S/D 922 may directly perform a test result output operation, or the test result output operation may be performed under control of the TCON 923.

Figure 20:
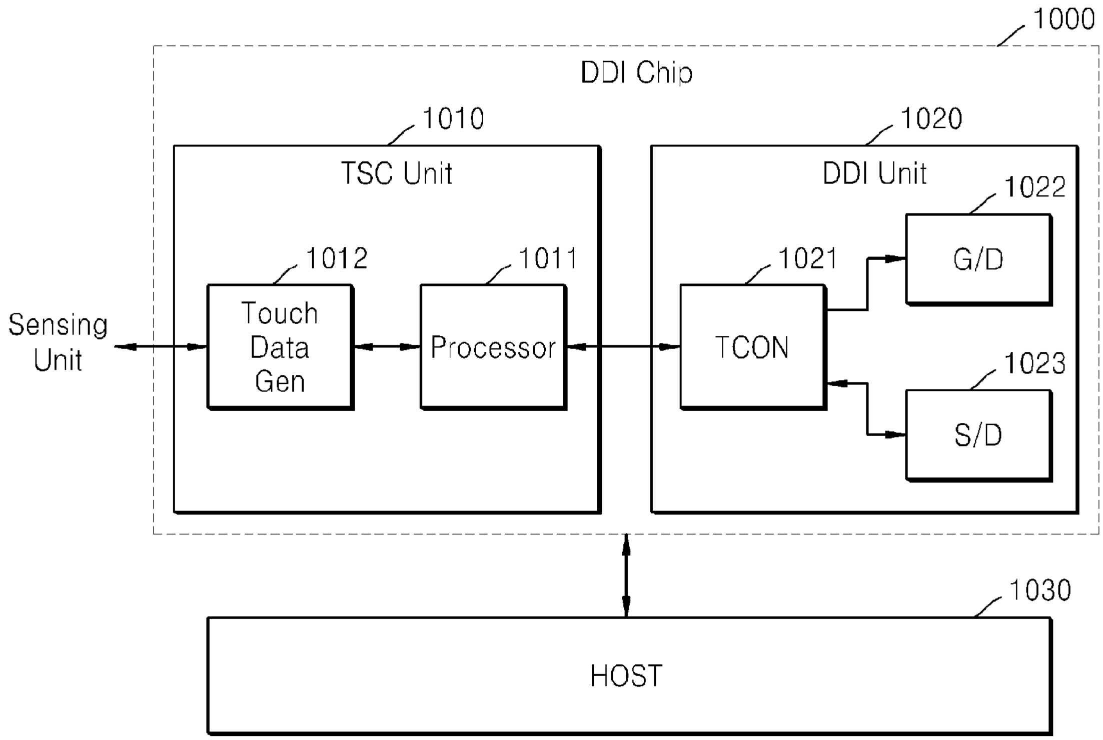
FIG. 20 is a block diagram of a DDI according to another exemplary embodiment of the inventive concept.

FIG. 20 is a block diagram of a DDI 1000 according to another exemplary embodiment of the inventive concept. FIG. 20 shows an example in which a touch controller is integrated in the DDI 1000.

In a display apparatus, to provide a touch sensing function, a touch panel may be included in the display apparatus together with a display panel, and a controller for a touch sensing operation may be integrated in a DDI as the same chip. As shown in FIG. 20, the DDI 1000 may include a touch screen controller (TSC) unit 1010 and a DDI unit 1020. The TSC unit 1010 may include a signal processor 1011 and a touch data generation unit 1012. The DDI unit 1020 may include a TCON 1021, a G/D 1022, and an S/D 1023 for realizing an image on a display panel (not shown). The DDI 1000 may communicate with an external host 1030.

The signal processor 1011 performs a general control operation of circuits in the TSC unit 1010. The touch data generation unit 1012 is electrically connected to a plurality of sensing units through a sensing line and generates a sensing signal by sensing a change in a capacitance of the plurality of sensing units according to a touch. In addition, the touch data generation unit 1012 generates and outputs touch data by processing the generated sensing signal. The signal processor 1011 or the host 1030 determines whether the touch is performed on a touch screen and determines a location where the touch is performed, by performing a predetermined logic computation on the basis of the touch data.

The DDI unit 1020 may perform the same error detection code generation operation and error detection operation as the embodiments described above. For example, the TCON 1021 generates code data from display data and provides a data sequence, including the display data and the code data, to the S/D 1023 through a main link. The S/D 1023 performs an error detection operation using the received code data and may provide an error counting result to the TCON 1021.

As described above, the TSC unit 1010 and the DDI unit 1020 may be integrated in one chip, and accordingly, at least one piece of information may be transmitted and received between the TSC unit 1010 and the DDI unit 1020. For example, at least one piece of timing information to be used to drive the display panel may be provided to the TSC unit 1010, and the TSC unit 1010 may generate touch data by using the received timing information. The timing information may be generated by the TCON 1021 or directly generated by the host 1030.

Figure 21:
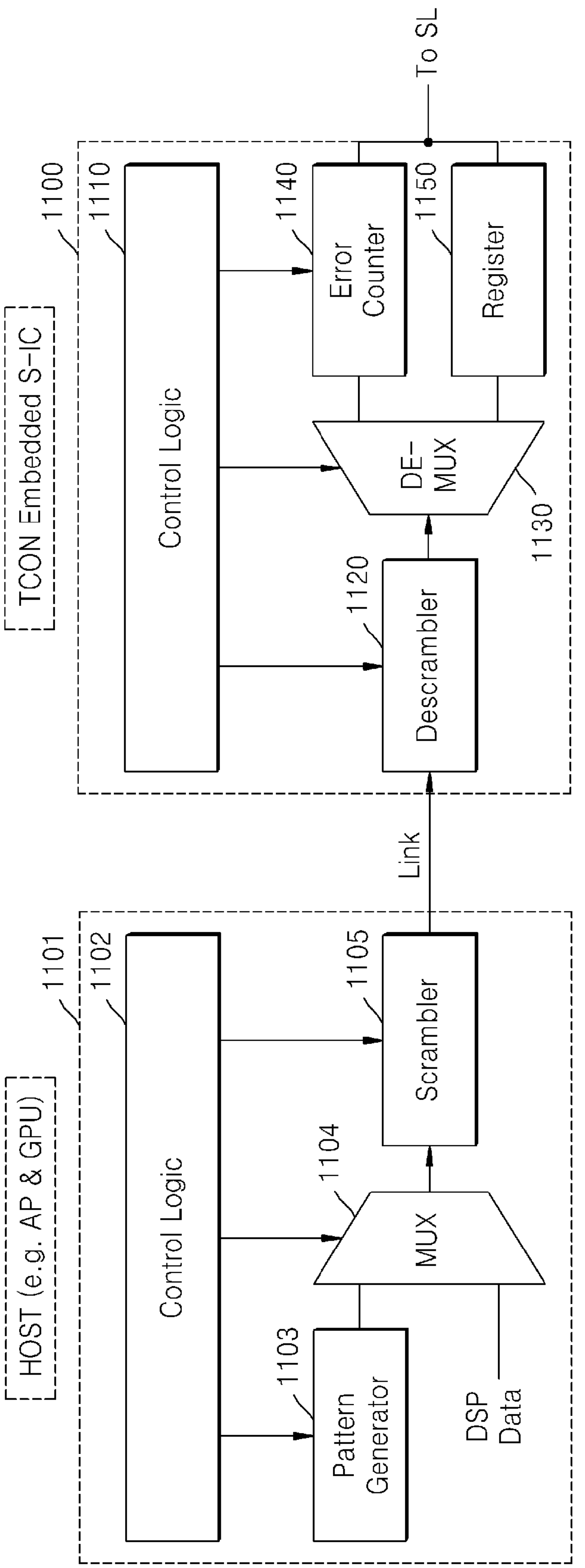
FIGS. 21 and 22 are block diagrams of timing controller embedded source drivers according to embodiments of the inventive concept.
Figure 22:
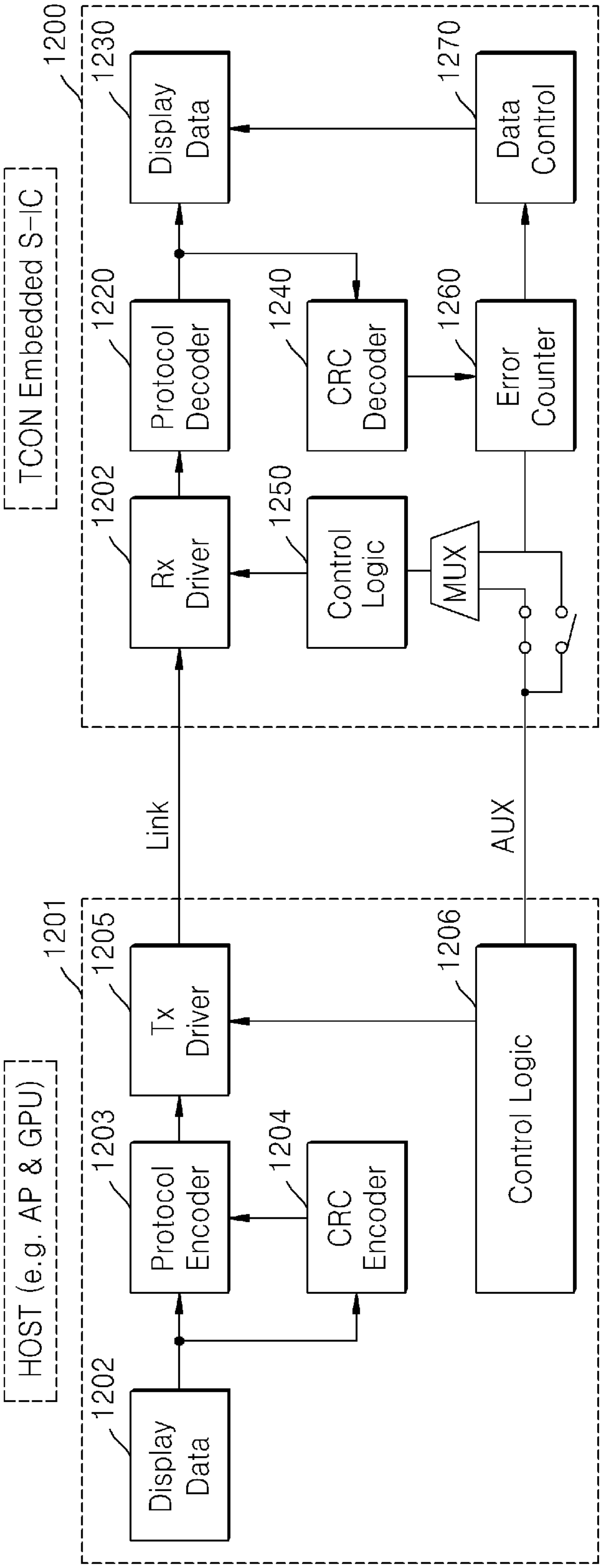

FIGS. 21 and 22 are block diagrams of TCON embedded S/Ds (hereinafter, referred to as TCON embedded S-ICs) 1100, 1200 according to exemplary embodiments of the inventive concept, respectively. FIG. 21 shows an example in which a BERT test on a main link is performed, and FIG. 22 shows an example in which a test using a CRC code according to the embodiments described above is performed.

As described above, a DDI may be defined in various ways. For example, the DDI may include at least one of a TCON, a G/D, and an S/D. As another example, the TCON may be implemented as a single chip by being embedded in the S/D, and cases where the TCON is embedded in the S/D according to embodiments of the inventive concept will now be described.

The operations of the TCON, which have been described in the embodiments described above, may be performed by a host 1101, 1201 (e.g., an application processor, a graphics processor, or the like). For example, an operation of generating a test pattern in a BERT mode and an operation of generating a CRC code as in the embodiments described above may be performed by the host 1101, 1201. The TCON embedded S-IC 1100, 1200 according to an exemplary embodiment of the inventive concept may perform an error detection operation and provide an error detection result (e.g., a result obtained by counting the number of errors) to the host 1101, 1201.

As shown in FIG. 21, the TCON embedded S-IC 1100 may include a control logic 1110, a descrambler 1120, a demultiplexer 1130, an error counter 1140, and a register 1150. FIG. 21 also shows the host 1101 which communicates with the TCON embedded S-IC 1100. The host 1101 may include a control logic 1102, a pattern generator 1103, a multiplexer 1104, and a scrambler 1105.

The host 1101 may randomize (or scramble) data so that data transmitted through a link is not weakened due to electromagnetic interference. Under control of the control logic 1102, display data DSP Data or a test pattern may be provided to the scrambler 1105. When a test mode is performed, the multiplexer 1104 may selectively output the test pattern, and the scrambler 1105 may scramble the test pattern.

The TCON embedded S-IC 1100 performs a normal display operation or a test operation using the test pattern under control of the control logic 1110. The descrambler 1120 descrambles the received test pattern, and the descrambled test pattern is provided to the error counter 1140 and the register 1150 via the demultiplexer 1130 under control of the control logic 1110.

The TCON embedded S-IC 1100 analyzes the received test pattern to determine whether an error exists. For example, the descrambled test pattern may have the same value as the test pattern generated by the pattern generator 1103 in the host 1101. The descrambled test pattern is provided to the error counter 1140, and the error counter 1140 counts data bits that are different from an expected value of the descrambled test pattern. The counting result of the error counter 1140 may be provided to the outside.

As shown in FIG. 22, at least one of the embodiments described above may be applied to the TCON embedded S-IC 1200. As shown in FIG. 22, the TCON embedded S-IC 1200 may include a reception driver 1210, a protocol decoder 1220, a data storage unit 1230, a CRC decoder 1240, a control logic 1250, an error counter 1260, and a data control unit 1270. FIG. 22 also shows the host 1201 which communicates with the TCON embedded S-IC 1200. The host 1201 may include a storage unit 1202 for temporarily storing display data, a protocol encoder 1203 for converting data according to a transmission protocol, a transmission driver 1205 for transmitting a packet including a data sequence, and a CRC encoder 1204 for generating an error detection code from the display data. In addition, through a channel AUX other than a main link Link, information stored in registers (not shown) of the host 1201 and the TCON embedded S-IC 1200 may be shared. The host 1201 may further include a control logic 1206, and the control logic 1206 may receive information from the TCON embedded S-IC 1200 through the channel AUX and control a transmission operation of the transmission driver 1205 on the basis of the received information.

As shown in FIG. 22, a CRC data generation operation using display data and an operation of packetizing a data sequence, including the display data and CRC data, may be performed by the host 1201. Also, the packet may be transmitted by the host 1201. In addition, as in the embodiments described above, an error detection operation, an operation of transmitting an error counting result as a test result, and a self error result output operation or an error result output operation according to a control from the outside may be performed by the TCON embedded S-IC 1200. An error counting result may be provided to the host 1201 through the channel AUX instead of the main link Link. A separate control signal for a control operation on the TCON embedded S-IC 1200 may be provided to the control logic 1250 in the TCON embedded S-IC 1200 through the channel AUX and a multiplexer (not shown). The control logic 1250 in the TCON embedded S-IC 1200 may control a reception operation through the main link Link in response to the control signal from the host 1201.

Figure 23:
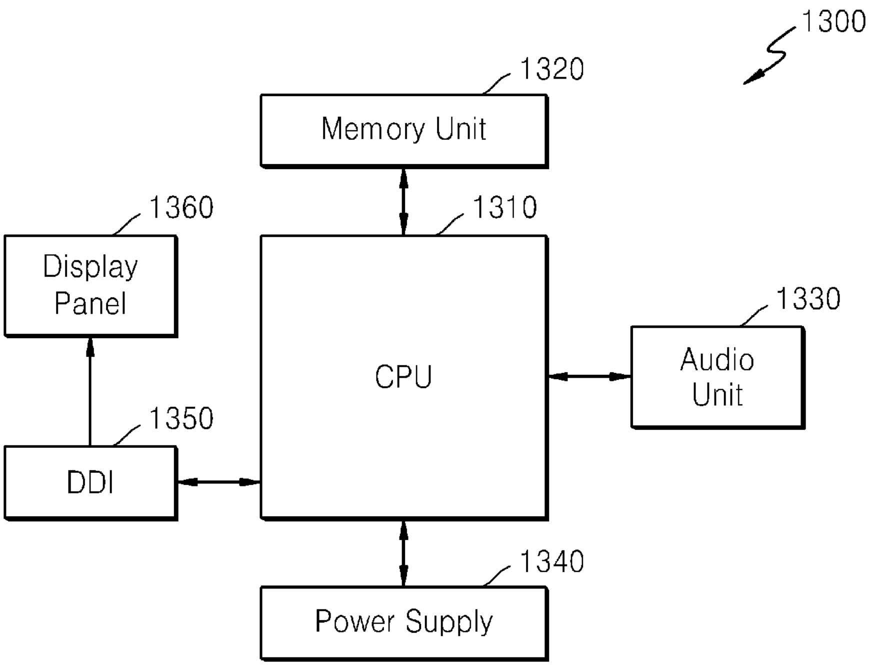
FIG. 23 is a block diagram of user equipment including a DDI, according to an exemplary embodiment of the inventive concept.

FIG. 23 is a block diagram of user equipment 1300 including a DDI 1350, according to an exemplary embodiment of the inventive concept. As shown in FIG. 23, the user equipment 1300 may include a central processing unit (CPU) 1310, a memory unit 1320, an audio unit 1330, a power supply unit 1340, the DDI 1350, and a display panel 1360.

The CPU 1310 controls the general operation of the user equipment 1300. For example, the CPU 1310 may control a booting operation of the user equipment 1300 when power is applied. Alternatively, the CPU 1310 may drive firmware for controlling the user equipment 1300. The firmware may be loaded and driven in the memory unit 1320.

The memory unit 1320 may include a volatile memory device, such as a dynamic random access memory (DRAM), or a nonvolatile memory device, such as read only memory (ROM) or a flash memory device. For example, the memory unit 1320 may store an operating system, an application program, firmware, and the like for driving the user equipment 1300. In addition, the volatile memory device in the memory unit 1320 may load the operating system, the application program, the firmware, and the like under control of the CPU 1310.

The audio unit 1330 may reproduce voice data under control of the CPU 1310, and the power supply unit 1340 provides power required to drive the user equipment 1300. The DDI 1350 may perform an error detection code generation operation and an error detection operation as in the embodiments described above. For example, the DDI 1350 may include a TCON and an S/D. The TCON generates code data from display data and provides a data sequence, including the display data and the code data, to the S/D through a main link. The S/D performs an error detection operation using the received code data and may provide an error counting result to the TCON. A test result according to the error detection operation may be displayed on the display panel 1360 under control of the DDI 1350.

While the inventive concept has been particularly shown and described with reference to exemplary embodiments thereof, it will be understood that various changes in form and details may be made therein without departing from the spirit and scope of the following claims.

What is claimed is:

1. A timing controller comprising:

a code generation unit configured to generate a first code from display data;

a protocol encoder configured to generate a data sequence, including the display data and the first code; and a transmission unit configured to provide the data sequence to a source driver, wherein the first code is an error detection code, wherein the timing controller is configured to receive a data error detection result, the data error detection result is generated from the source driver based on a data error detection operation on the display data using the first code.

2. The timing controller of claim 1, wherein the data sequence further includes first information for enabling the data error detection operation.

3. The timing controller of claim 1, wherein the code generation unit is a cyclic redundancy check (CRC) encoder for generating CRC data from the display data and the first code includes the CRC data.

4. The timing controller of claim 1, wherein:
the timing controller is configured to sequentially provide the display data for a screen output with respect to a plurality of gate lines included in a panel to the source driver, and
the code generation unit is configured to generate the first code in correspondence with the display data for each gate line.

5. The timing controller of claim 1, wherein the timing controller is configured to sequentially provide the display data for a screen output with respect to a plurality of gate lines included in a panel to the source driver and receive the data error detection result using the first code from the source driver after providing the display data for the plurality of gate lines.

6. The timing controller of claim 1, further comprising:
a reception unit configured to receive the data error detection result using the first code from the source driver; and
a data control unit configured to control a combination of the display data and test data based upon the data error detection result.

7. The timing controller of claim 1, wherein the timing controller is connected to a plurality of source drivers through a plurality of links and is configured to simultaneously provide the data sequence to the plurality of source drivers.

8. A display driver integrated circuit (DDI) comprising:
a timing controller configured to generate a first code from display data and output a data sequence including the display data and the first code; and
a first source driver configured to receive the data sequence through a first link, generate a second code corresponding to the display data, and perform an error detection operation on the display data by using the first code included in the data sequence and the second code,
wherein the first code is a first error detection code,
wherein the second code is a second error detection code, and
wherein the error detection operation compares the first code with the second code to determine whether an error occurs in the display data.

9. The DDI of claim 8, wherein the timing controller comprises:
a code generation unit configured to generate the first code from the display data;
a protocol encoder configured to generate the data sequence including the display data and the first code; and
a transmission unit configured to provide the data sequence to the first source driver through the first link.

10. The DDI of claim 8, wherein the timing controller and the first source driver are integrated in the same chip.

11. The DDI of claim 8, wherein an error detection result received from the first source driver is output to a panel.

12. The DDI of claim 11, wherein the timing controller is configured to combine the display data and the error detection result, and to provide combined information of the display data and the error detection result to the first source driver.

13. The DDI of claim 11, wherein the source driver includes a switch control logic configured to generate a control signal that controls an information transmission direction of the first link to transmit the error detection result.

14. The DDI of claim 8, further comprising:
a second source driver, and
wherein the timing controller is configured to simultaneously transmit each respective data sequence to the first source driver through the first link and to the second source driver through the second link.

15. The DDI of claim 8, wherein the first source driver comprises:
a protocol decoder configured to receive and decode the data sequence; and
an error detection unit configured to perform an error detection operation on the display data by using the first code included in the data sequence and the second code calculated from the display data.

16. The DDI of claim 15, wherein the source driver includes:
a code decoder configured to generate the second code by performing computations using the display data; and
a comparator configured to compare the first code with the second code to determine whether the error occurs in the display data.

17. The DDI of claim 16, wherein the error detection unit includes:
a counting unit configured to count a number of errors based upon a result of the comparison from the comparator; and
a register configured to store a result of the counting.

18. A method of operating a display driver integrated circuit (DDI), comprising:
generating by a timing controller a first code corresponding to first display data, wherein the first code is an error detection code;
enabling first information indicating a request for error detection using the first code and the first display data;
generating by the timing controller a first data sequence including the enabled first information, the first code, and the first display data;
providing the first data sequence to a source driver through a link between the timing controller and the source driver; and
comparing by the source driver the first code with a second code generated from the first display data to determine whether an error occurs in the first display data.

19. The method of claim 18, further comprising:
counting a number of errors based upon a result of the comparison; and
providing an error number counting result to the timing controller when second information for requesting to transmit an error detection result is enabled.

20. The method of claim 19, further comprising:
generating test data based upon the error number counting result;
generating a second data sequence including second display data and the test data; and outputting normal display based upon the second display data and a test result on the test data.

* * * * *